United States Patent
Furukawa

(10) Patent No.: US 11,040,712 B2
(45) Date of Patent: Jun. 22, 2021

(54) INFORMATION PROCESSING APPARATUS AND INFORMATION PROCESSING METHOD

(71) Applicant: SONY CORPORATION, Tokyo (JP)

(72) Inventor: Ryosuke Furukawa, Tokyo (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 16/498,629

(22) PCT Filed: Mar. 30, 2018

(86) PCT No.: PCT/JP2018/013631
§ 371 (c)(1),
(2) Date: Sep. 27, 2019

(87) PCT Pub. No.: WO2018/190152
PCT Pub. Date: Oct. 18, 2018

(65) Prior Publication Data
US 2020/0094737 A1 Mar. 26, 2020

(30) Foreign Application Priority Data
Apr. 14, 2017 (JP) .............................. JP2017-080437

(51) Int. Cl.
*B60W 30/08* (2012.01)
*B60W 30/09* (2012.01)
(Continued)

(52) U.S. Cl.
CPC ............ *B60W 30/08* (2013.01); *B60W 30/09* (2013.01); *A61B 5/00* (2013.01); *A61B 5/18* (2013.01);
(Continued)

(58) Field of Classification Search
CPC .... B60W 30/08; B60W 30/09; B60W 30/095; B60W 30/0953; B60W 30/0956;
(Continued)

(56) References Cited

U.S. PATENT DOCUMENTS 9,165,326 B1 10/2015 He et al.
9,469,298 B2 * 10/2016 Hayasaka .............. G08G 1/166
(Continued)

FOREIGN PATENT DOCUMENTS

CA 2832670 A1 6/2014
EP 2743118 A1 6/2014
(Continued)

OTHER PUBLICATIONS

International Search Report and Written Opinion of PCT Application No. PCT/JP2018/013631, dated Jun. 26, 2018, 08 pages of ISRWO.

Primary Examiner — Van T Trieu
(74) Attorney, Agent, or Firm — Chip Law Group

(57) ABSTRACT

The present technology relates to an information processing apparatus, an information processing method, and a program which are possible to enable the user to reliably avoid a risk. The information processing apparatus includes a presentation control unit that generates a risk avoidance proposal for a user on the basis of a predicted risk, an evaluating unit that evaluates a level of obedience of the user on the basis of response of the user to the risk avoidance proposal, and a risk predicting unit that adjusts a risk prediction parameter on the basis of the evaluated level of obedience. The present technology can be applied to, for example, an information processing system or an information processing apparatus which assists driving of a mobile body, or an information processing system or an information processing apparatus which provides various kinds of insurances.

12 Claims, 11 Drawing Sheets

(51) Int. Cl.
  *A61B 5/18* (2006.01)
  *A61B 5/00* (2006.01)
  *B60Q 9/00* (2006.01)
  *G06Q 40/08* (2012.01)
(52) U.S. Cl.
  CPC ............ *A61B 5/486* (2013.01); *A61B 5/4833* (2013.01); *A61B 5/7275* (2013.01); *A61B 5/7282* (2013.01); *B60Q 9/00* (2013.01); *G06Q 40/08* (2013.01)
(58) Field of Classification Search
  CPC ................ B60W 40/00; B60W 40/08; B60W 2040/0818; B60W 2040/0827; B60W 2040/0836; B60W 2040/0845; B60W 2040/0854; B60W 2040/0863; B60W 2040/0872; B60W 50/08; B60W 50/085; B60W 50/0097; B60W 50/10; B60W 50/14; G06Q 40/08; G08G 1/16; B60R 25/25; G06K 9/00
  See application file for complete search history.

(56) References Cited

U.S. PATENT DOCUMENTS

| | | | |
|---|---|---|---|
| 9,472,102 B2* | 10/2016 | McClain | G08G 1/16 |
| 2003/0187704 A1* | 10/2003 | Hashiguchi | G06Q 40/08 |
| | | | 705/4 |
| 2014/0336896 A1* | 11/2014 | Udaka | B60T 7/22 |
| | | | 701/70 |
| 2015/0166059 A1* | 6/2015 | Ko | B60T 7/22 |
| | | | 701/28 |
| 2016/0001781 A1* | 1/2016 | Fung | G16H 50/20 |
| | | | 701/36 |
| 2016/0086393 A1 | 3/2016 | Collins et al. | |

FOREIGN PATENT DOCUMENTS

| | | |
|---|---|---|
| JP | 10-080405 A | 3/1998 |
| JP | 2003-281375 A | 10/2003 |
| JP | 2015-099465 A | 5/2015 |
| JP | 2016-140377 A | 8/2016 |

* cited by examiner

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2018/013631 filed on Mar. 30, 2018, which claims priority benefit of Japanese Patent Application No. JP 2017-080437 filed in the Japan Patent Office on Apr. 14, 2017. Each of the above-referenced applications is hereby incorporated herein by reference in its entirety.

TECHNICAL FIELD

The present technology relates to an information processing apparatus, an information processing method, and a program, and, particularly, relates to an information processing apparatus, an information processing method, and a program which are suitable for use in a case where a risk avoidance proposal is presented to a user.

BACKGROUND ART

Conventionally, biological information of a driver has been used to detect a state of the driver during driving.

For example, a proposal has been made in which a measurement value of skin impedance of a driver is corrected using correction data based on a measurement value of skin impedance of the driver while the driver is at rest and is closing his/her eyes, and an average value of measurement values while the driver is in a normal active state, and a level of wakefulness of the driver is judged on the basis of the corrected value (see, for example, Patent Document 1).

For example, a proposal has been made in which biological data measured with a biological sensor of a vehicle is transmitted to a data processing apparatus via a mobile terminal provided at an in-vehicle charger and a public network, and the data processing apparatus transmits the received biological data to the mobile terminal of a driver (see, for example, Patent Document 2).

Then, for example, driving assistance for avoiding a risk such as an accident is performed on the basis of the detected state of the driver.

CITATION LIST

Patent Document

Patent Document 1: Japanese Patent Application Laid-Open No. H10-80405
Patent Document 2: Japanese Patent Application Laid-Open No. 2016-140377

SUMMARY OF THE INVENTION

Problems to be Solved by the Invention

By the way, even if driving assistance is performed, there is a case where a risk cannot be avoided in a case where a user does not behave as intended.

The present technology has been made in view of such circumstances, and is directed to enabling the user to reliably avoid a risk.

Solutions to Problems

An information processing apparatus according to an aspect of the present technology includes: a presentation control unit configured to generate a risk avoidance proposal for a user on the basis of a predicted risk; an evaluating unit configured to evaluate a level of obedience of the user on the basis of response of the user to the risk avoidance proposal; and a risk predicting unit configured to adjust a risk prediction parameter on the basis of the evaluated level of obedience.

The risk predicting unit may predict a risk regarding driving of a mobile body by the user.

A driving behavior detecting unit configured to detect driving behavior which is behavior of the user or the mobile body during driving may further be included, and the risk predicting unit may predict the risk on the basis of a detection result of the driving behavior.

A level of dangerous driving behavior, which is to be detected by the driving behavior detecting unit, may change on the basis of the level of obedience.

As the level of obedience becomes lower, the level of dangerous driving behavior, which is to be detected by the driving behavior detecting unit, may become lower.

A diagnosis unit configured to diagnose aptitude of the user for driving on the basis of at least one of a state of the user before driving or a state of the user during driving may further be included, and the risk predicting unit may predict the risk on the basis of a result of the diagnosis.

As the level of obedience becomes lower, a level of a risk, which is to be predicted by the risk predicting unit, may become lower.

An insurance fee calculating unit configured to calculate an insurance fee of an insurance for the user on the basis of the level of obedience may further be included.

The insurance fee calculating unit may lower the insurance fee as the level of obedience is higher and increases the insurance fee as the level of obedience is lower.

The risk is a risk regarding driving of a vehicle by the user, and the insurance may include an automobile insurance.

An information processing method according to an aspect of the present technology includes: a presentation control step of generating a risk avoidance proposal for a user on the basis of a predicted risk; an evaluation step of evaluating a level of obedience of the user on the basis of response of the user to the risk avoidance proposal; and a risk prediction step of adjusting a risk prediction parameter on the basis of the evaluated level of obedience.

A program according to an aspect of the present technology for causing a computer to execute processing includes: a presentation control step of generating a risk avoidance proposal for a user on the basis of a predicted risk; an evaluation step of evaluating a level of obedience of the user on the basis of response of the user to the risk avoidance proposal; and a risk prediction step of adjusting a risk prediction parameter on the basis of the evaluated level of obedience.

In an aspect of the present technology, a risk avoidance proposal for a user is generated on the basis of a predicted risk, a level of obedience of the user is evaluated on the basis of response of the user to the risk avoidance proposal, and a risk prediction parameter is adjusted on the basis of the evaluated level of obedience.

Effects of the Invention

According to one aspect of the present technology, it is possible to obtain a level of obedience of a user. As a result, for example, it is possible to enable the user to reliably avoid a risk using the level of obedience of the user.

Note that the advantageous effects described here are not necessarily limitative, and any of the advantageous effects described in the present disclosure may be attained.

MODE FOR CARRYING OUT THE INVENTION

Figure 1:
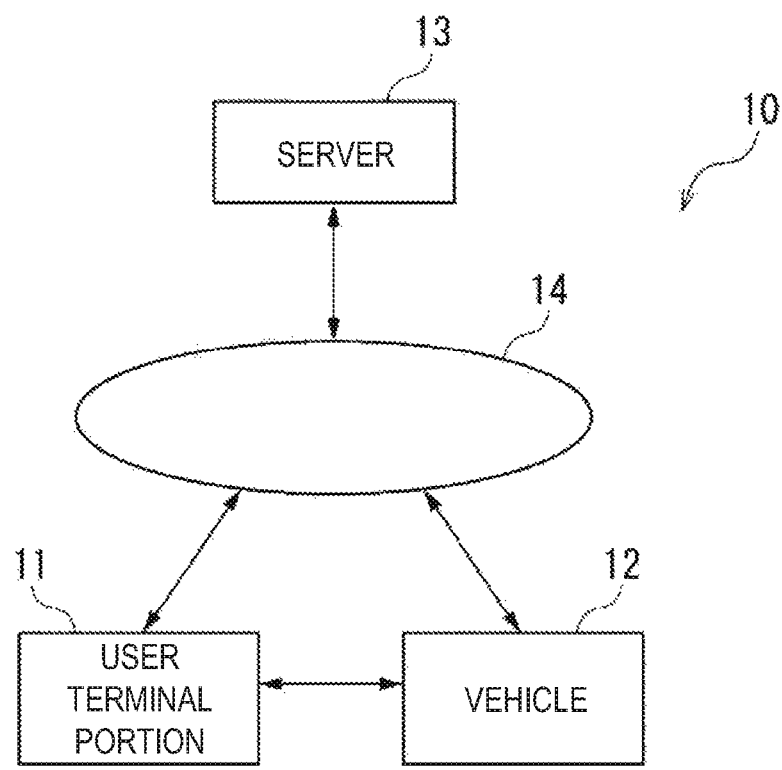
FIG. 1 is a block diagram illustrating an embodiment of an information processing system to which the present technology is applied.

An embodiment for implementing the present technology will be described below. The description will be provided in the following order.
1. Embodiment
2. Modified Examples
3. Other 1. Embodiment Configuration Example of Information Processing System FIG. 1 is a block diagram illustrating an embodiment of an information processing system to which the present technology is applied.

An information processing system 10 is, for example, a system which provides service such as driving assistance of a vehicle and an automobile insurance using a telematics technology.

The information processing system 10 includes a user terminal portion 11, a vehicle 12, and a server 13. The user terminal portion 11 and the vehicle 12 perform communication with each other directly or via a network 14. The server 13 performs communication with the user terminal portion 11 and the vehicle 12 via the network 14.

The user terminal portion 11 includes one or more information processing terminals possessed by a user who utilizes the information processing system 10. For example, the user terminal portion 11 can include a mobile terminal and a wearable terminal.

The vehicle 12 is a vehicle driven by the user who utilizes the information processing system 10.

The server 13 provides service such as driving assistance and an automobile insurance to the user who utilizes the information processing system 10 by performing communication with the user terminal portion 11 and the vehicle 12 via the network 14.

Note that, while, FIG. 1 illustrates one user terminal portion 11, one vehicle 12, and one server 13 to make it easy to understand the drawing, it is also possible to provide two or more user terminal portions 11, two or more vehicles 12, and two or more servers 13. For example, the number of the user terminal portions 11 and the number of the vehicles 12 which are provided are substantially equal to the number of users who utilize the information processing system 10.

Further, to facilitate explanation, description of "via the network 14" in a case where the user terminal portion 11, the vehicle 12, and the server 13 perform communication via the network 14 will be omitted below.

Configuration Example of User Terminal Portion

Figure 2:
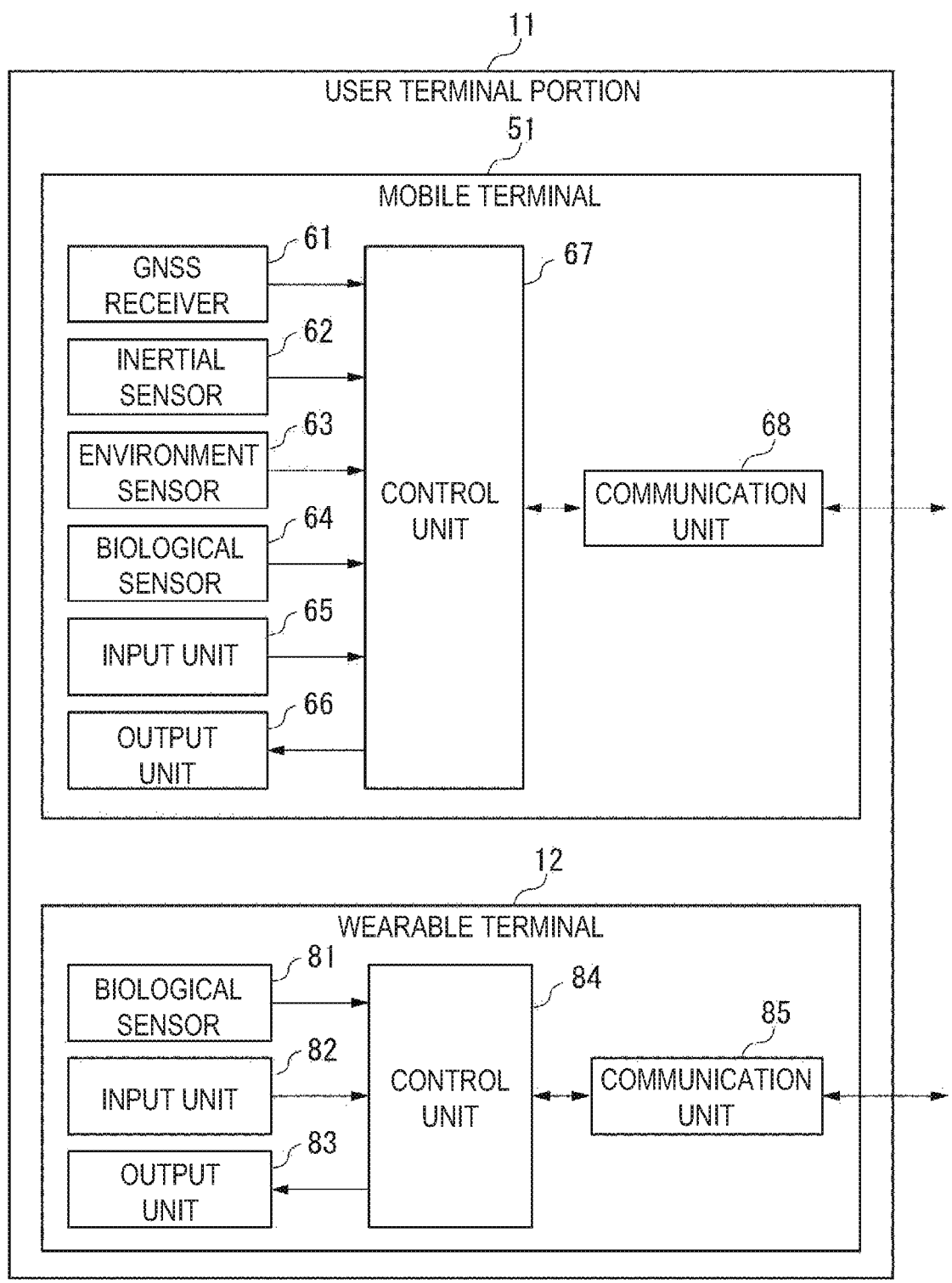
FIG. 2 is a block diagram illustrating a configuration example of a user terminal portion.

FIG. 2 is a block diagram illustrating a configuration example of the user terminal portion 11. In this example, the user terminal portion 11 includes a mobile terminal 51 and a wearable terminal 52.

The mobile terminal 51 is a mobile information processing terminal such as, for example, a smartphone, a mobile phone, a tablet, a notebook personal computer, portable game machine, a portable moving image, or music reproduction apparatus.

The mobile terminal 51 includes a global navigation satellite system (GNSS) receiver 61, an inertial sensor 62, an environment sensor 63, a biological sensor 64, an input unit 65, an output unit 66, a control unit 67, and a communication unit 68.

The GNSS receiver 61 measures a current location of (a user who possesses) the mobile terminal 51 by receiving a radio wave from a positioning satellite and supplies location data indicating the measured current location to the control unit 67.

The inertial sensor 62 detects various kinds of inertial data regarding (the user who possesses) the mobile terminal 51 and supplies the detected inertial data to the control unit 67. The inertial data detected by the inertial sensor 62 includes one or more types of data among, for example, acceleration, angular velocity, or the like.

The environment sensor 63 detects various kinds of environmental data around (the user who possesses) the mobile terminal 51, and supplies the detected environmental data to the control unit 67. The environmental data detected by the environment sensor 63 includes one or more types of data among, for example, earth magnetism, an atmosphere pressure, carbon dioxide concentration, or the like.

The biological sensor 64 detects various kinds of biological data of the user and supplies the detected biological data to the control unit 67. The biological data detected by the biological sensor 64 includes one or more types of data among, for example, a heart rate, a perspiration amount, a blood pressure, a blood oxygen level, muscle potential, a body temperature, body composition, breath alcohol content, maximum oxygen intake, calorie consumption, voice tone, conversation speed, or the like.

The input unit 65 includes an input device for inputting various kinds of data to the mobile terminal 51. For example, the input unit 65 includes one or more types among a button, a switch, a key, a touch panel, a microphone, or the like. The input unit 65 supplies input data to the control unit 67.

The output unit 66 includes an output device for outputting various kinds of information and data. For example, the output unit 66 includes one or more types among a display, a speaker, a buzzer, a vibrator, or the like.

The control unit 67 includes, for example, a control device such as various kinds of processors. The control unit 67 performs control of the respective units of the mobile terminal 51 and various kinds of processing on the basis of data supplied from the GNSS receiver 61, the inertial sensor 62, the environment sensor 63, the biological sensor 64, and the input unit 65 and data received from outside via the communication unit 68, or the like. Further, the control unit 67 supplies data obtained through various kinds of processing to the output unit 66 or transmits the data to other equipment via the communication unit 68.

The communication unit 68 performs communication with other equipment (such as, for example, the vehicle 12, the server 13, and the wearable terminal 52) using a predetermined communication scheme. As the communication scheme of the communication unit 68, an arbitrary wireless or wired scheme can be employed. Further, the communication unit 68 can support a plurality of communication schemes.

The wearable terminal 52 is, for example, a wearable terminal in an arbitrary form such as a spectacle type, a wristwatch type, a bracelet type, a necklace type, a neckband type, an earphone type, a headset type, and a head-mounted type.

The wearable terminal 52 includes a biological sensor 81, an input unit 82, an output unit 83, a control unit 84, and a communication unit 85.

The biological sensor 81 detects various kinds of biological data of the user in a similar manner to the biological sensor 64 of the mobile terminal 51 and supplies the detected biological data to the control unit 84. Note that types of the biological data detected by the biological sensor 81 may overlap with types of the biological data detected by the biological sensor 64 of the mobile terminal 51.

The input unit 82 includes an input device for inputting various kinds of data to the wearable terminal 52. For example, the input unit 82 includes one or more types among, for example, a button, a switch, a key, a touch panel, a microphone, or the like. The input unit 82 supplies input data to the control unit 67.

The output unit 83 includes an output device for outputting various kinds of information and data. For example, the output unit 83 includes one or more types among a display, a speaker, a buzzer, a vibrator, or the like.

The control unit 84 includes, for example, a control device such as various kinds of processors. The control unit 84 performs control of the respective units of the wearable terminal 52 and various kinds of processing on the basis of data supplied from the biological sensor 81 and the input unit 82, data received from outside via the communication unit 85, or the like. Further, the control unit 84 supplies data obtained through various kinds of processing to the output unit 83 or transmits the data to other equipment via the communication unit 85.

The communication unit 85 performs communication with other equipment (such as, for example, the vehicle 12, the server 13, and the mobile terminal 51) using a predetermined communication scheme. As the communication scheme of the communication unit 85, an arbitrary wireless or wired scheme can be employed. Further, the communication unit 85 can support a plurality of communication schemes.

Configuration Example of Vehicle

Figure 3:
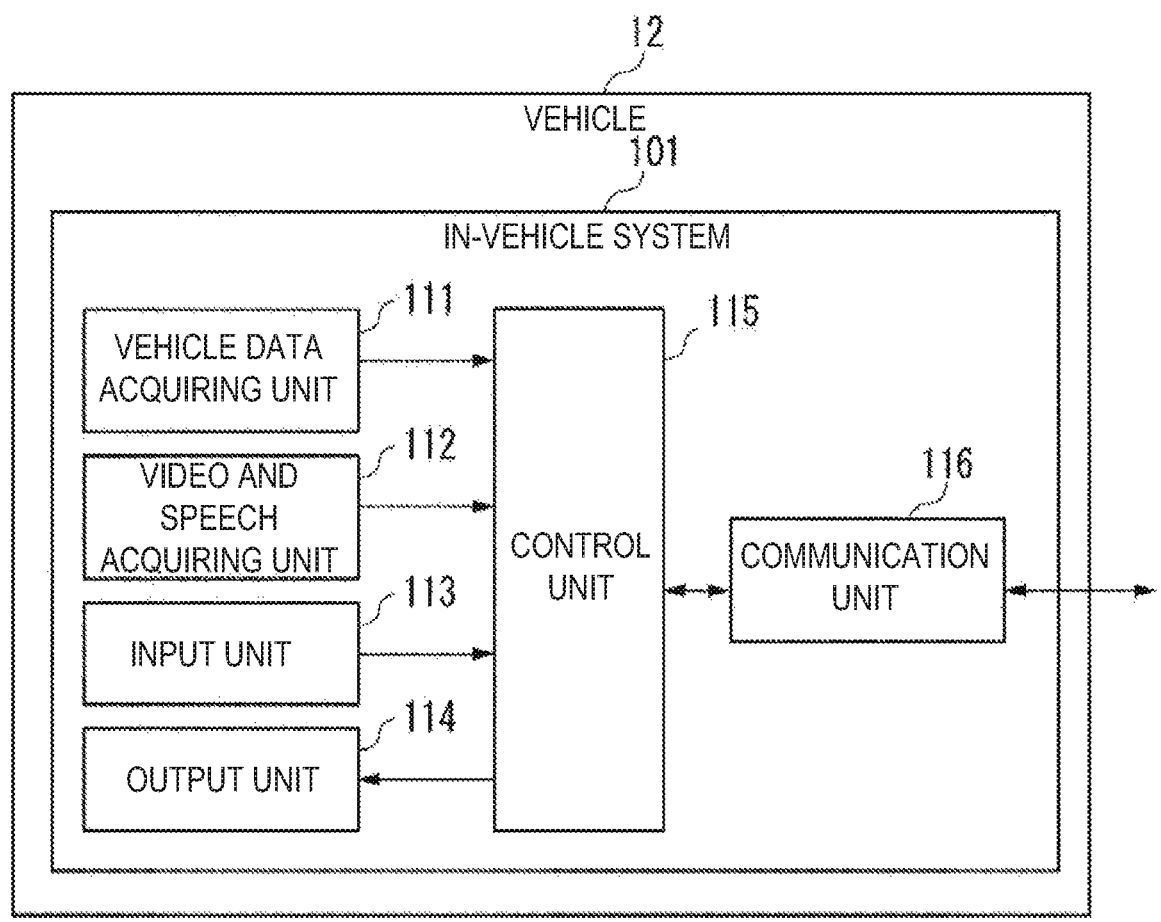
FIG. 3 is a block diagram illustrating a configuration example of a vehicle.

FIG. 3 is a block diagram illustrating a configuration example of part of the vehicle 12. The vehicle 12 includes an in-vehicle system 101. The in-vehicle system 101 includes a vehicle data acquiring unit 111, a video and speech acquiring unit 112, an input unit 113, an output unit 114, a control unit 115, and a communication unit 116.

The vehicle data acquiring unit 111 includes, for example, various kinds of sensors, communication equipment, a control device, or the like. The vehicle data acquiring unit 111 acquires vehicle data regarding the vehicle 12 and supplies the acquired vehicle data to the control unit 115. The vehicle data acquired by the vehicle data acquiring unit 111 includes one or more types of data among, for example, vehicle speed, torque, a steering angle, a yaw angle, a state of a gear, a state of an emergency brake, a stepping-in amount of an accelerator pedal, a stepping-in amount of a brake pedal, a state of a direction indicator, a state of a light, a rotation angle and rotation speed of a tire, data indicating a diagnosis result of on-board diagnostics (OBD) (hereinafter, referred to as OBD data), sensor data of a millimeter wave radar, a laser radar, or the like, or the like.

The video and speech acquiring unit 112 includes, for example, a camera, a microphone, or the like. The camera provided at the video and speech acquiring unit 112 may be a special camera such as, for example, a time of flight (ToF) camera, a stereo camera, and an infrared camera as well as a normal camera. The video and speech acquiring unit 112, for example, acquires video and speech around and inside of the vehicle 12 and supplies video data and speech data indicating the acquired video and speech to the control unit 115.

The input unit 113 includes an input device for inputting various kinds of data to the vehicle 12. For example, the input unit 113 includes one or more types among a button, a switch, a key, a touch panel, or the like. The input unit 113 supplies input data to the control unit 115.

The output unit 114 includes an output device for outputting various kinds of information and data. For example, the output unit 114 includes one or more types among a display (for example, a head-up display), a speaker, a buzzer, a vibrator, an instrument panel, or the like.

The control unit 115 includes, for example, a control device such as an electronic control unit (ECU). The control unit 115 performs control of the respective units of the vehicle 12 and various kinds of processing on the basis of data supplied from the vehicle data acquiring unit 111, the video and speech acquiring unit 112, and the input unit 113, data received from outside via the communication unit 116, or the like. Further, the control unit 115 supplies data obtained through various kinds of processing to the output unit 114 or transmits the data to other equipment via the communication unit 116.

The communication unit 116 performs communication with other equipment (such as, for example, the server 13, the mobile terminal 51, and the wearable terminal 52) using a predetermined communication scheme. As the communication scheme of the communication unit 116, an arbitrary wireless or wired scheme can be employed. Further, the communication unit 116 can support a plurality of communication schemes.

Configuration Example of Server

Figure 4:
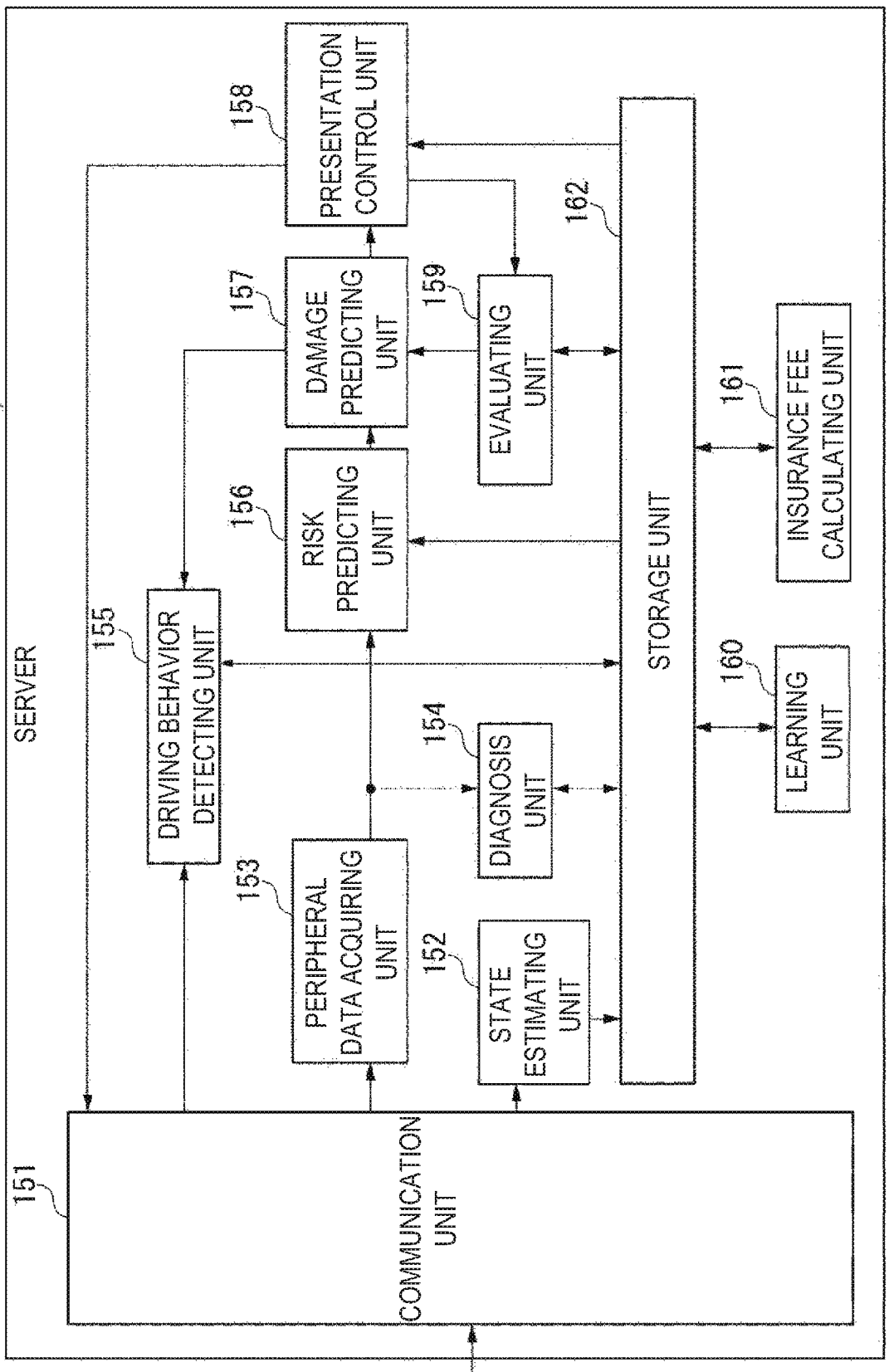
FIG. 4 is a block diagram illustrating a configuration example of a server.

FIG. 4 is a block diagram illustrating a configuration example of the server 13. The server 13 includes a communication unit 151, a state estimating unit 152, a peripheral data acquiring unit 153, a diagnosis unit 154, a driving behavior detecting unit 155, a risk predicting unit 156, a damage predicting unit 157, a presentation control unit 158, an evaluating unit 159, a learning unit 160, an insurance fee calculating unit 161, and a storage unit 162.

The communication unit 151 performs communication with other equipment (such as, for example, the vehicle 12, the mobile terminal 51, the wearable terminal 52, and other servers (not illustrated)) via the network 14 using a predetermined communication scheme. As the communication scheme of the communication unit 151, an arbitrary wireless or wired scheme can be employed. Further, the communication unit 151 can support a plurality of communication schemes.

The state estimating unit 152 acquires data regarding a state of the user from the user terminal portion 11 and the vehicle 12 via the communication unit 151. The state estimating unit 152 generates and updates a state data log which is a log of data regarding the state of the user and stores the state data log in the storage unit 162.

Further, the state estimating unit 152 performs estimation processing of the state of the user using a state estimation model stored in the storage unit 162 on the basis of the state data log. Here, the state estimation model is a model to be used for estimating the state of the user, and is, for example, generated for each user. The state estimating unit 152 generates and updates estimated state history which is history of estimation results of the state of the user and stores the estimated state history in the storage unit 162.

The peripheral data acquiring unit 153 acquires peripheral data indicating a peripheral state of the vehicle 12 on the basis of the data received from the user terminal portion 11, the vehicle 12, and other servers (not illustrated) via the communication unit 151. The peripheral data acquiring unit 153 supplies the acquired peripheral data to the diagnosis unit 154 and the risk predicting unit 156.

The diagnosis unit 154 acquires the estimated state history, driving behavior history, and a driving diagnosis model of the user from the storage unit 162. Here, the driving behavior history is history of detection results of driving behavior which is behavior of the user or the vehicle 12 during driving, and is, for example, generated for each user. Further, the driving diagnosis model is a model to be used for driving diagnosis which diagnoses user's aptitude of driving of the vehicle, and is, for example, generated for each user. The diagnosis unit 154 diagnoses driving of the user using the driving diagnosis model on the basis of the acquired history. The diagnosis unit 154 generates and updates the driving diagnosis history which is history of the driving diagnosis result of the user and stores the driving diagnosis history in the storage unit 162.

The driving behavior detecting unit 155 receives data from the user terminal portion 11 and the vehicle 12 via the communication unit 151. Further, the driving behavior detecting unit 155 acquires the estimated state history of the user and a driving behavior detection model from the storage unit 162. Here, the driving behavior detection model is a model to be used for detecting driving behavior, and is, for example, generated for each user. Further, the driving behavior detecting unit 155 acquires a risk regarding driving of the vehicle by the user and a prediction result of a damage which may occur by the risk from the damage predicting unit 157. The driving behavior detecting unit 155 performs processing of detecting driving behavior of the user using the driving behavior detection model on the basis of the acquired history, data, or the like. The driving behavior detecting unit 155 generates and updates driving behavior history which is history of detection results of the driving behavior of the user and stores the driving behavior history in the storage unit 162.

The risk predicting unit 156 acquires the estimated state history, the driving diagnosis history, the driving behavior history, and a risk prediction model of the user from the storage unit 162. Here, the risk prediction model is a model to be used for predicting a risk regarding driving of the vehicle 12 by the user, and is, for example, generated for each user. The risk predicting unit 156 predicts a risk using the risk prediction model on the basis of the acquired history. The risk predicting unit 156 supplies a prediction result of the risk to the damage predicting unit 157.

The damage predicting unit 157 predicts a damage occurring by the risk predicted by the risk predicting unit 156 while using a level of obedience of the user evaluated by the evaluating unit 159 as necessary. Here, the level of obedience is a level that the user obediently follows a proposal, or the like, from the server 13. The damage predicting unit 157 supplies prediction results of a risk and a damage to the driving behavior detecting unit 155 and the presentation control unit 158.

The presentation control unit 158 acquires the driving diagnosis history of the user and an insurance fee calculated by the insurance fee calculating unit 161 from the storage unit 162. The presentation control unit 158 generates feedback information to be presented to the user, including information regarding the predicted risk on the basis of the prediction results of the risk and the damage, the driving diagnosis history of the user, and the insurance fee. The presentation control unit 158 controls presentation of the feedback information to the user by transmitting the generated feedback information to the user terminal portion 11 of the user or the vehicle 12 via the communication unit 151. Further, the presentation control unit 158 supplies the feedback information to the evaluating unit 159.

The evaluating unit 159 acquires the estimated state history and the driving behavior history of the user from the storage unit 162. Then, the evaluating unit 159 evaluates the level of obedience of the user on the basis of the acquired history and the feedback information. The evaluating unit 159 supplies the level of obedience of the user to the damage predicting unit 157 and stores the level of obedience in the storage unit 162.

The learning unit 160 acquires the estimated state history of the user from the storage unit 162. The learning unit 160 learns a pattern of a normal state (hereinafter, referred to as a normal state pattern) of the user on the basis of the acquired estimated state history and stores data indicating the obtained normal state pattern in the storage unit 162.

Further, the learning unit 160 acquires the estimated state history of each user included in a predetermined user aggregate from the storage unit 162. The learning unit 160 learns a pattern of an average state of users within the user aggregate (hereinafter, referred to as a user aggregate state pattern) on the basis of the acquired estimated state history and stores data indicating the obtained user aggregate state pattern in the storage unit 162.

Further, the learning unit 160 acquires the state data log, the estimated state history, the driving diagnosis history, and the driving behavior history of the user from the storage unit 162. The learning unit 160 learns the state estimation model, the driving diagnosis model, the driving behavior detection model, and the risk prediction model on the basis of the acquired log and history and stores the models in the storage unit 162.

The insurance fee calculating unit 161 acquires the driving diagnosis history, the driving behavior history, and the level of obedience of the user from the storage unit 162. The insurance fee calculating unit 161 calculates an insurance fee of an automobile insurance of the user on the basis of the acquired history and level of obedience. The insurance fee calculating unit 161 stores data indicating the calculated insurance fee in the storage unit 162.

Driving Assistance Processing

Figure 5:
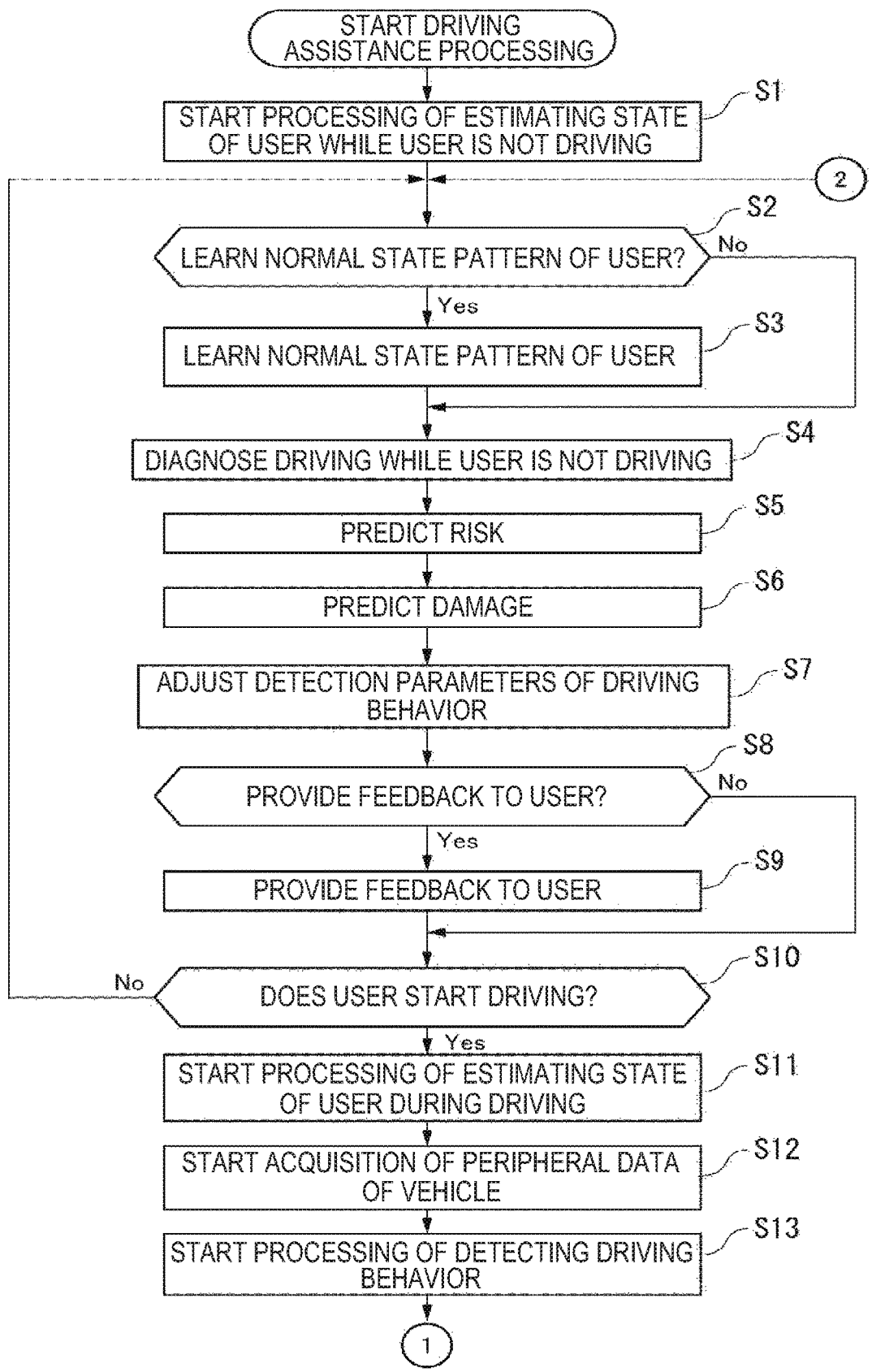
FIG. 5 is a flowchart for explaining driving assistance processing to be executed by the server.
Figure 6:
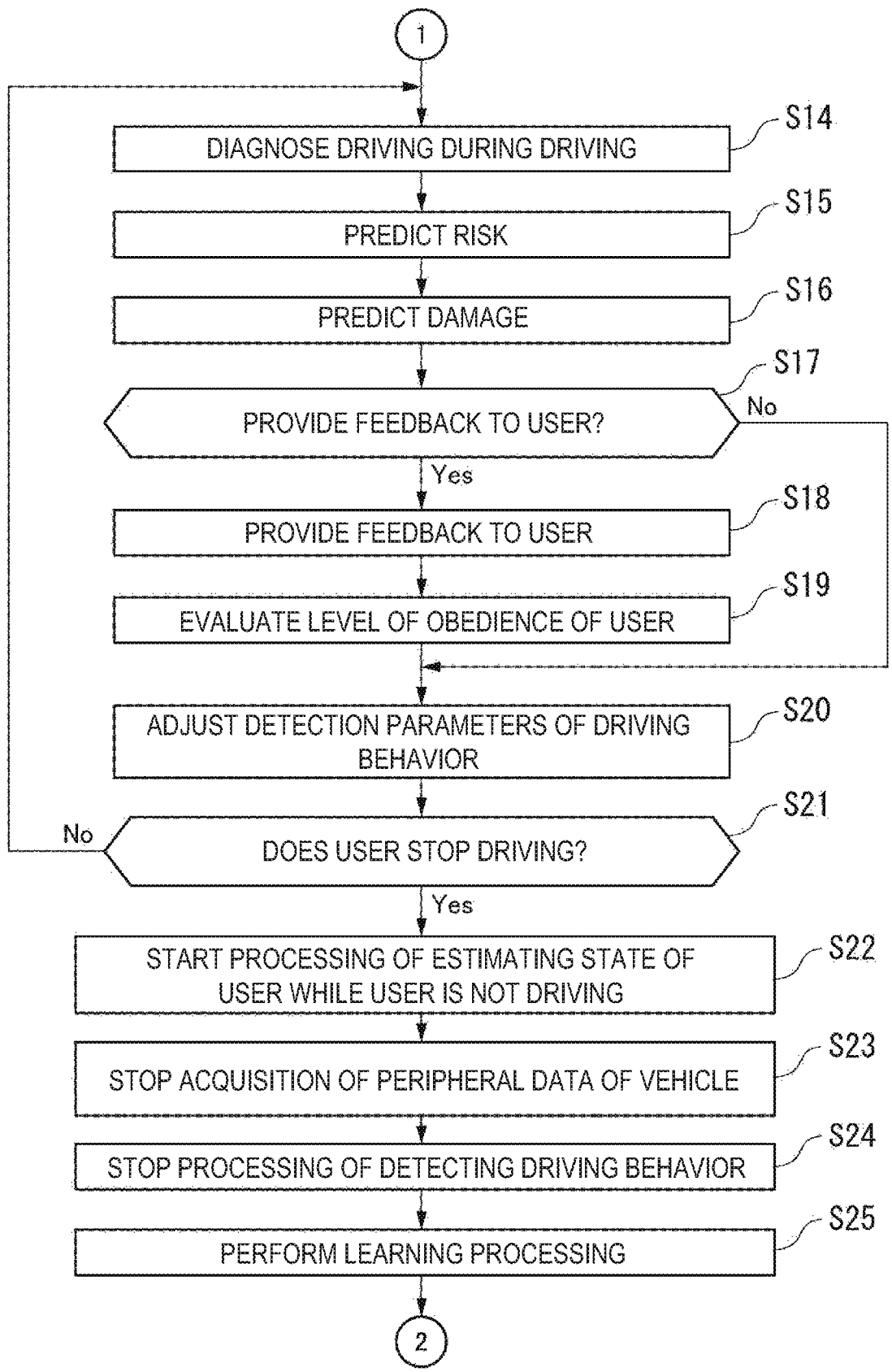
FIG. 6 is a flowchart for explaining the driving assistance processing to be executed by the server.

Driving assistance processing to be executed by the server 13 will be described next with reference to the flowcharts in FIG. 5 and FIG. 6.

Note that, while processing to be performed on one specific user (hereinafter, referred to as a target user) will be mainly described below, actually, processing on users other than the target user is performed in parallel.

In step S1, the server 13 starts processing of estimating a state of the user (target user) while the user is not driving. Specifically, for example, the following processing is started.

The state estimating unit 152 acquires data regarding the state of the target user from data (such as, for example, inertial data, environmental data, biological data, and input data) received by the communication unit 151 from the user terminal portion 11 of the target user. The state estimating unit 152 stores the respective pieces of data in the storage unit 162 along with time at which the respective pieces of data are acquired. By this means, the state data log of the target user is updated.

Note that the state data log of the target user is not only the data regarding the state of the target user himself/herself and can include data regarding a peripheral state of the target user.

The state estimating unit 152 estimates a current state of the target user using the state estimation model of the target user stored in the storage unit 162 on the basis of the state data log of the target user within the most recent predetermined period. For example, the state estimating unit 152 estimates a current biological state, behavior, and feeling of the target user as the current state of the target user.

Figure 7:
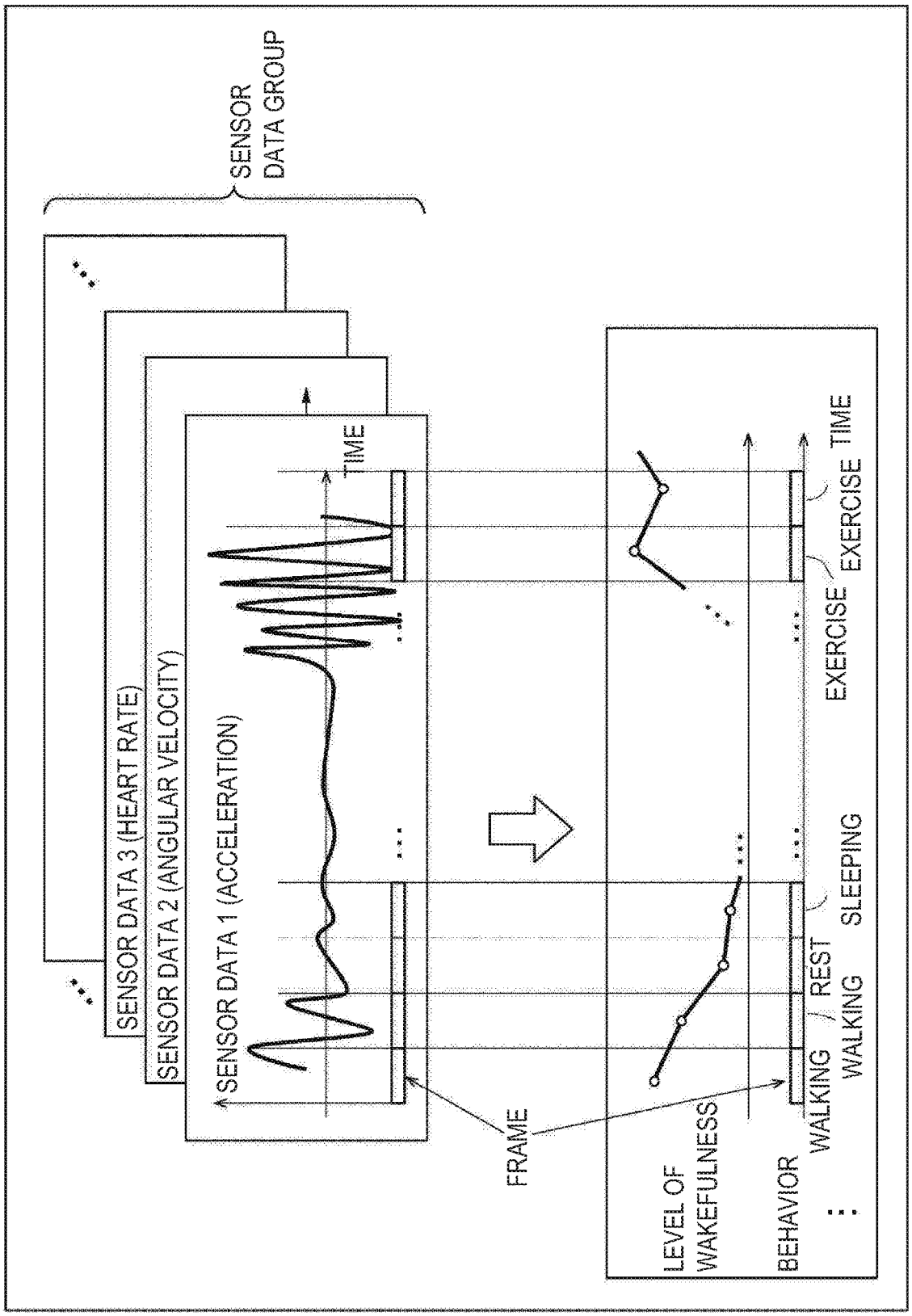
FIG. 7 is a diagram for explaining user state estimation processing.

For example, as illustrated in FIG. 7, the state estimating unit 152 estimates the biological state and the behavior of the target user for each frame of a predetermined period on the basis of time-series change of a sensor data group indicating the state of the target user. For example, various kinds of biological states of the target user such as a degree of concentration, a level of wakefulness, a degree of fatigue, a stress level, a tension level, and vigor of exercise are estimated on the basis of a heart rate, a perspiration amount, or the like, of the target user. For example, types of behavior of the target user (such as, for example, rest, walking, running, cycling, going up and down stairs, eating, and sleeping) are estimated on the basis of acceleration, angular velocity, an ambient atmospheric pressure, or the like, of the target user.

Further, for example, the state estimating unit 152 estimates a travel distance, moving speed, a range of activity, or the like, of the target user on the basis of location data, acceleration, or the like, of the target user.

Still further, the state estimating unit 152 estimates feeling of the target user on the basis of the biological data of the target user, the estimation result of the biological state of the target user, or the like. For example, the state estimating unit 152 estimates a degree of delight, anger, sorrow, and pleasure, a level of excitement, an irritation level, a level of anxiety, or the like, of the target user.

Note that the biological states and the feeling of the target user are not necessarily all clearly divided and some of them can overlap with each other. For example, the level of excitement can be either the biological state or the feeling of the target user.

Further, as the method for estimating the state of the user, an arbitrary method can be employed. Still further, types of the state of the user to be estimated are not limited to the above-described examples, and types can be added or deleted as necessary.

The state estimating unit 152 stores the estimated state of the target user in the storage unit 162 along with time at which the state is estimated. By this means, the estimated state history of the target user is updated.

Note that, for example, as illustrated in FIG. 7, the estimated state history includes data in which numerical values for each frame are arranged in chronological order like a level of wakefulness, and data in which labels (indicating types of behavior) provided for each frame are arranged in chronological order like behavior.

In step S2, the learning unit 160 determines whether or not to learn a normal state pattern (normal state pattern) of the user (target user). For example, learning of the normal state pattern of the target user is executed at a predetermined timing such as when the target user starts utilizing the information processing system 10, every time a predetermined period has elapsed, and every time a data amount of the estimated state history of the target user increases by equal to or greater than a predetermined amount. Then, in a case where it is a timing for learning the normal state pattern of the target user, the learning unit 160 determines to learn the normal state pattern of the target user, and the processing proceeds to step S3.

Figure 8:
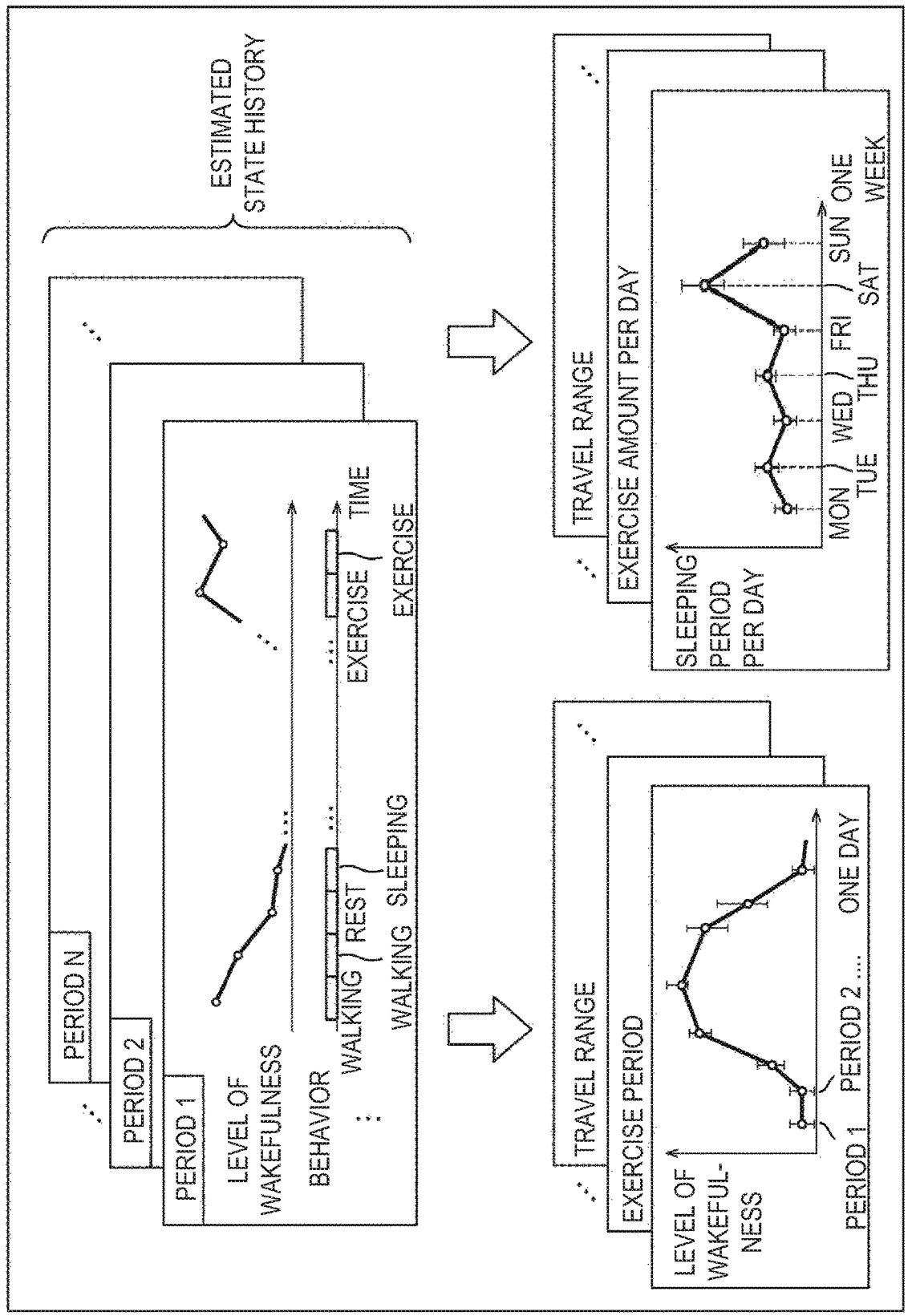
FIG. 8 is a diagram for explaining a method for learning a user normal state pattern.

In step S3, the learning unit 160 learns the normal state pattern (normal state pattern) of the user (target user). For example, as illustrated in FIG. 8, the learning unit 160 learns the normal state pattern of the target user on the basis of the estimated state history within a most recent relatively long period (for example, on a monthly basis, on a yearly basis) of the target user.

For example, the learning unit 160 learns a transition pattern indicating normal transition of a predetermined period (for example, 1 day) of each item by calculating an average, dispersion, or the like, for each predetermined period (for example, 1 minute, 10 minutes, 30 minutes, or 1 hour) of the following each item as the normal state pattern of the target user. For example, normal transition patterns of a degree of concentration, a level of wakefulness, a degree of fatigue, a stress level, a tension level, vigor of exercise, a heart rate, a perspiration amount, an exercise amount, a degree of delight, anger, sorrow, and pleasure, a level of excitement, an irritation level, a level of anxiety, or the like, of the target user of one day are learned.

Further, for example, the learning unit 160 learns a normal transition pattern for each predetermined period (for example, one week) of each item by calculating an average, dispersion, or the like, for each day (for each day of week) of the following each item as the normal state pattern of the target user. For example, normal transition patterns of a sleeping period, awakening time, bedtime, an exercise amount, a travel range, the number of times of meal, mealtime, a mealtime slot, a driving period, a driving time slot, a commuting time slot, a commuting time slot to school, or the like, of one week are learned.

Further, the learning unit 160 learns an average normal state pattern within a user aggregate (user aggregate state pattern) on the basis of estimated state history of the respective users within a predetermined user aggregate, so as to be compared with the normal state pattern of the target user.

Here, the user aggregate may include all users of the information processing system 10 or may include only part of the users. In the latter case, for example, the user aggregate may include users who are similar to the target user. Here, the users who are similar to the target user are, for example, users whose attributes (such as, for example, age, sex, job, and address), behavior patterns, preference, or the like, are similar to those of the target user. Further, the target user may be included or not included in the user aggregate.

Figure 9:
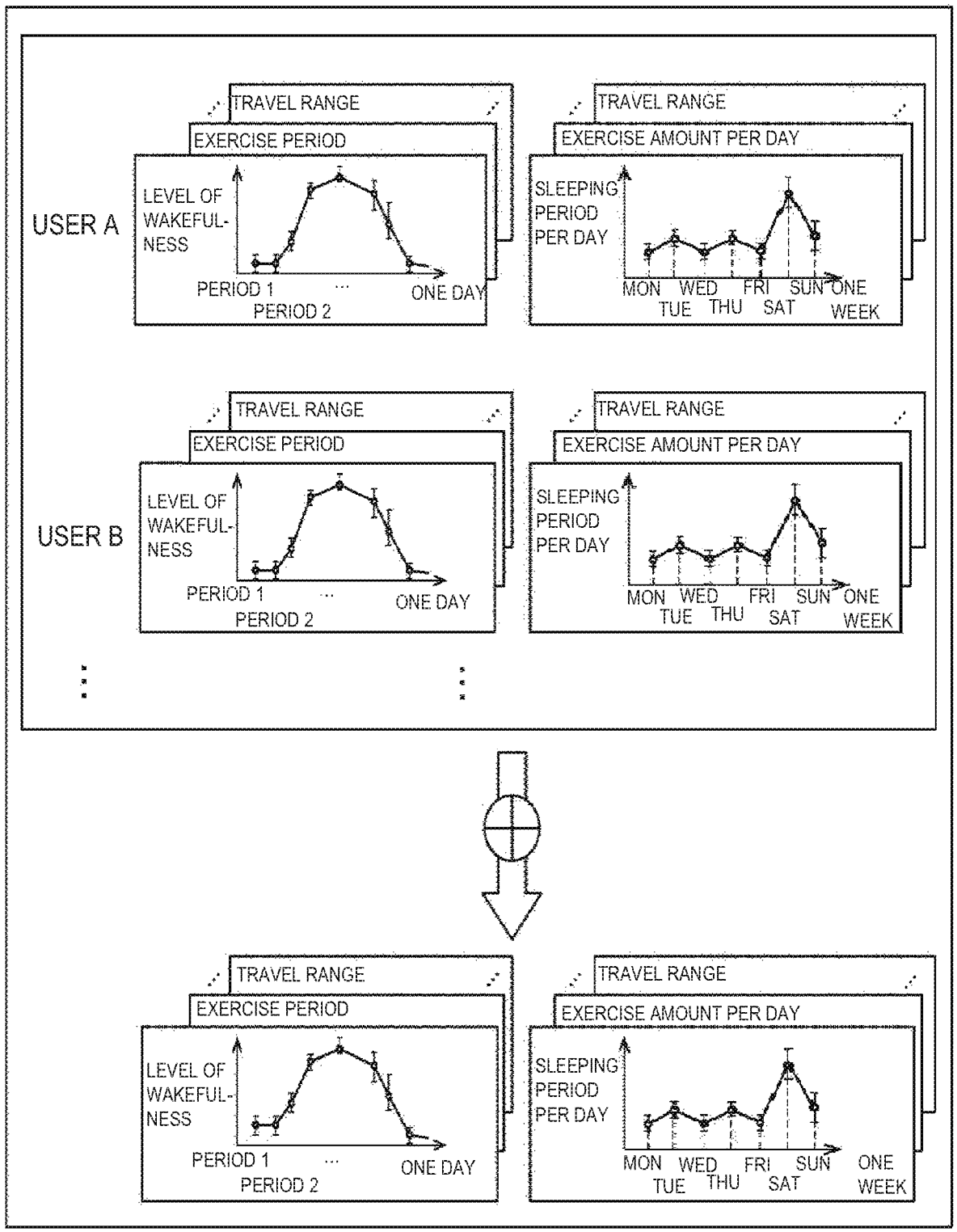
FIG. 9 is a diagram for explaining a method for learning a user aggregate state pattern.

For example, as illustrated in FIG. 9, the learning unit 160 learns the user aggregate state pattern by tallying an average of the normal state patterns of the respective users within the user aggregate. For example, by the average of the normal transition patterns of one day of each item being tallied within the user aggregate, an average transition pattern of one day of each item within the user aggregate is learned. Further, for example, by an average normal transition pattern of one week of each item being tallied within the user aggregate, an average transition pattern of one week of each item within the user aggregate is learned.

The learning unit 160 stores data indicating learning results of the normal state pattern of the target user and the user aggregate state pattern in the storage unit 162.

Note that a timing at which the normal state pattern of the target user is learned does not necessarily have to be synchronized with a timing at which the user aggregate state pattern is learned, and the learning may be performed at different timings.

Then, the processing proceeds to step S4.

Meanwhile, in step S2, in a case where it is determined not to learn the normal state pattern of the target user, the processing in step S3 is skipped, and the processing proceeds to step S4.

In step S4, the diagnosis unit 154 performs driving diagnosis while the driver is not driving. For example, the diagnosis unit 154 detects a transition pattern (hereinafter, referred to as a most recent state pattern) within a most recent relatively short period (for example, one day and one week) for items which are the same as the items of the above-described normal state pattern on the basis of the estimated state history of the target user.

Figure 10:
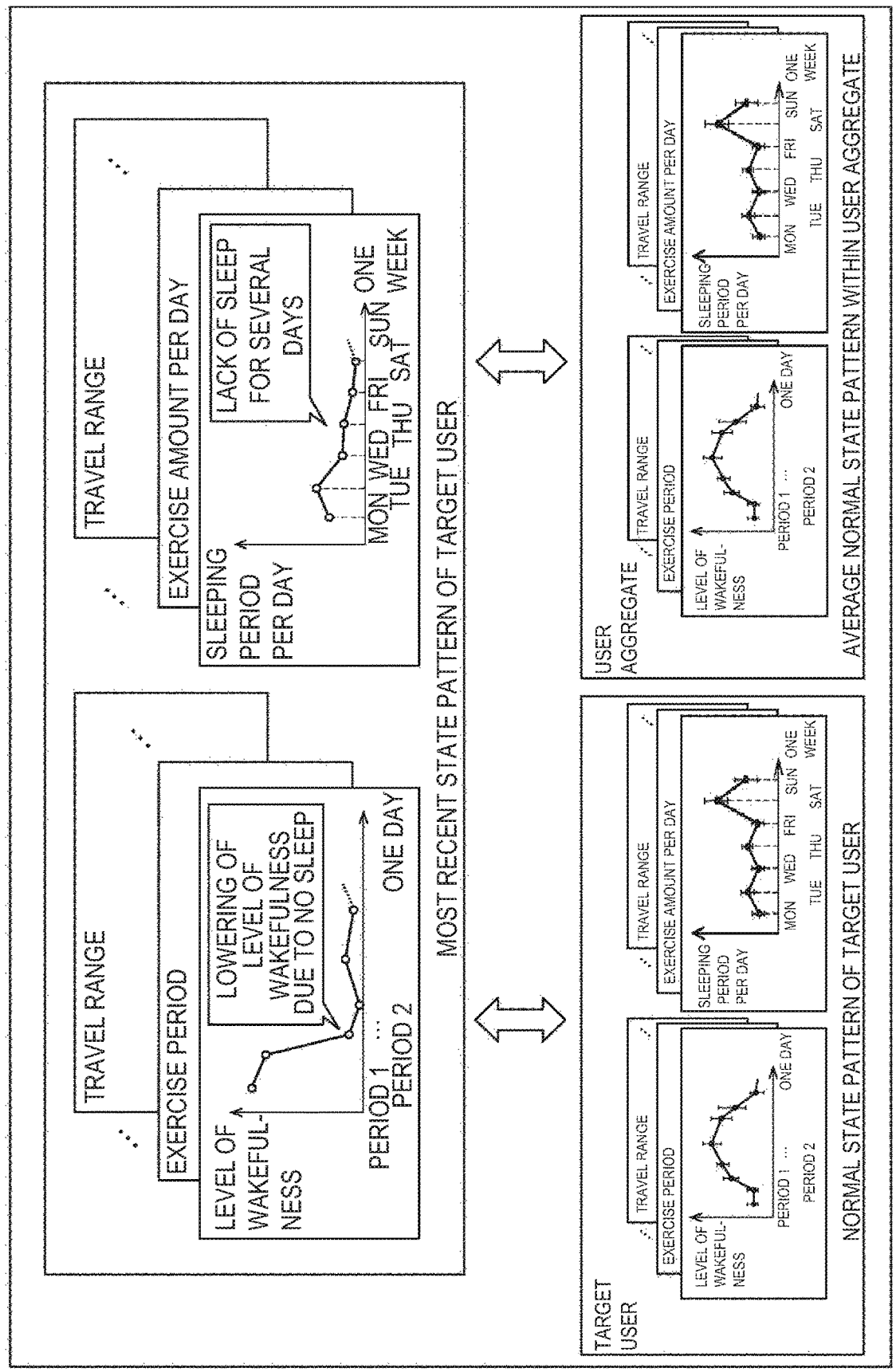
FIG. 10 is a diagram for explaining an example of a method for diagnosing driving.

The diagnosis unit 154 then, for example, calculates a divergence degree vector x indicating a degree of divergence between the most recent state pattern of the target user and the normal state pattern, and a divergence degree vector y indicating a degree of divergence between the most recent state pattern of the target user and the user aggregate state pattern as illustrated in FIG. 10. For example, the divergence degree vector x and the divergence degree vector y are set as vectors indicating values obtained by normalizing degrees of divergence for each item between two state patterns which are to be compared.

The diagnosis unit 154 then calculates driving aptitude u while the target user is not driving using a driving diagnosis model of the target user expressed with a function f in the following expression (1).

$$u = f(x, y, wx, wy) \quad (1)$$

Note that wx is weight for the divergence degree vector x, and wy is weight for the divergence degree vector y.

The driving aptitude u becomes greater as the degree of divergence of each item included in the divergence degree vector x becomes smaller. That is, as the most recent state pattern of the target user is closer to the normal state pattern, in other words, a difference between the most recent state of the target user and the normal state is smaller, it is determined that the state is more appropriate for driving. Meanwhile, the driving aptitude u becomes smaller as the degree of divergence of each item included in the divergence degree vector x becomes greater. That is, as the most recent state pattern of the target user is farther from the normal state pattern, in other words, a difference between the most recent state of the target user and the normal state is greater, it is determined that the state is less appropriate for driving.

Further, the driving aptitude u becomes greater as the degree of divergence of each item included in the divergence degree vector y becomes smaller. That is, as the most recent state pattern of the target user is closer to the user aggregate state, in other words, a difference between the most recent state of the target user and the average state in the user aggregate is smaller, it is determined that the state is more appropriate for driving. Meanwhile, the driving aptitude u becomes smaller as the degree of divergence of each item included in the divergence degree vector y becomes greater. That is, as the most recent state pattern of the target user is farther from the user aggregate state pattern, in other words, a difference between the most recent state of the target user and the average state in the user aggregate is greater, it is determined that the state is less appropriate for driving.

Note that, as the weight wx becomes greater, influence of the divergence degree vector x (that is, a difference between the most recent state pattern of the target user and the normal state pattern) with respect to the driving aptitude u becomes greater. Meanwhile, as the weight wy becomes greater, influence of the divergence degree vector y (that is, a difference between the user aggregate state pattern of the target user and the normal state pattern) with respect to the driving aptitude u becomes greater.

Further, for example, in a case where the driving aptitude u is less than a predetermined threshold, the diagnosis unit 154 estimates a cause of lowering of the driving aptitude u. For example, the diagnosis unit 154 extracts an item in which a product of the weight wx and the degree of divergence is equal to or greater than a predetermined value in the divergence degree vector x. Further, the diagnosis unit 154 extracts an item in which a product of the weight wy and the degree of divergence is equal to or greater than a predetermined value in the divergence degree vector y. The diagnosis unit 154 then estimates a cause of lowering of the driving aptitude u by comparing the most recent state pattern and the normal state pattern or the user aggregate average pattern for each extracted item.

For example, in a case where the sleeping period in the most recent state pattern of the target user drastically falls below the normal state pattern or the user aggregate average pattern, lack of sleep is estimated as the cause of lowering.

For example, in a case where one or more among an exercise period, a heart rate and a perspiration amount in the most recent state pattern of the target user drastically exceed the normal state pattern or the user aggregate average pattern, physical exhaustion by heavy exercise is estimated as the cause of lowering.

For example, in a case where one or more among a stress level, a tension level and an irritation level in the most recent state pattern of the target user drastically exceed the normal state pattern or the user aggregate average pattern, irritation of the target user is estimated as the cause of lowering.

Note that, in a case where the driving aptitude u is equal to or greater than a predetermined threshold, for example, there is no particular cause of lowering of the driving aptitude u.

The diagnosis unit 154 stores the driving aptitude u and the estimated cause of lowering in the storage unit 162 as the diagnosis result of aptitude of driving of the target user along with time at which the diagnosis is made. By this means, the driving diagnosis history of the target user is updated.

In step S5, the risk predicting unit 156 predicts a risk. Specifically, the risk predicting unit 156 acquires the driving diagnosis history of the target user and the risk prediction model from the storage unit 162. The risk predicting unit 156 predicts a risk in a case where the target user performs driving at the present moment using the risk prediction model of the target user on the basis of the driving diagnosis history of the target user.

For example, in a case where the cause of lowering of the driving aptitude u is lack of sleep or physical exhaustion, it is estimated that there is a risk of drowsy driving.

For example, in a case where the cause of lowering of the driving aptitude u is irritation of the target user, for example, it is estimated that there is a risk of collision or contact with other vehicles due to excess speed, dangerous passing, or the like, collision, contact, or the like, with an obstacle (such as, for example, other vehicles, bicycles, and pedestrians) due to carelessness of the target user.

Further, the risk predicting unit 156 estimates a probability of occurrence of the predicted risk. For example, as the sleeping period of the target user is shorter, the estimated probability of occurrence of drowsy driving becomes higher.

Note that, typically, as the driving aptitude u is lower, the predicted risk and the probability of occurrence of the risk become greater.

The risk predicting unit 156 supplies a prediction result of the risk to the damage predicting unit 157. This prediction result of the risk includes the predicted risk, basis of prediction of the risk (for example, the cause of lowering of the driving aptitude u) and the probability of occurrence of the risk.

In step S6, the damage predicting unit 157 predicts damage. Specifically, the damage predicting unit 157 predicts damage (for example, a risk/penalty value) occurring by the risk predicted by the risk predicting unit 156. In this event, the probability of occurrence of the risk is taken into account. That is, as the probability of occurrence is higher, the predicted damage becomes greater, while as the probability of occurrence is lower, the predicted damage becomes smaller. The damage predicting unit 157 supplies prediction results of a risk and a damage to the driving behavior detecting unit 155 and the presentation control unit 158.

In step S7, the driving behavior detecting unit 155 adjusts detection parameters of driving behavior. For example, the driving behavior detecting unit 155 adjusts parameters for detecting dangerous driving among various kinds of driving behavior in accordance with the predicted risk and damage.

Here, the driving behavior relating to detection of dangerous driving is, for example, dangerous driving behavior such as sudden operation such as sudden starting, sudden acceleration, sudden braking, and sudden steering, driving in a zigzag, drowsy driving, lowering of a level of wakefulness and a degree of concentration, inattentive driving, distraction, excess speed, dangerous passing, lack of a distance between cars, and approach to an obstacle.

Further, the detection parameters are adjusted so that, as the estimated risk and damage become greater, a level of dangerous driving (a degree of risk) to be detected becomes lower. By this means, dangerous driving is detected in an earlier and minor stage.

For example, in a case where occurrence of drowsy driving is predicted, a threshold for the number of times of blink in drowsiness determination is set smaller so as to detect drowsiness of the user earlier. For example, in a case where occurrence of inattentive driving, distraction, excess speed, or the like, is predicted, a threshold for detecting sudden acceleration and sudden braking is set smaller to make it easier to detect sudden acceleration and sudden braking.

Still further, as the level of dangerous driving to be detected becomes lower, the level of the risk (degree of risk) to be predicted becomes lower. That is, a risk in an earlier and minor stage is predicted.

Here, the level of dangerous driving to be detected and the level of the risk to be predicted change in accordance with the driving aptitude u of the target user. For example, as described above, typically, as the driving aptitude u becomes lower, the predicted risk and the probability of occurrence of the damage become greater, and the predicted damage also becomes greater. Therefore, the detection parameters are adjusted so that the level of dangerous driving to be detected becomes further lower. As a result, as the driving aptitude u becomes lower, the level of dangerous driving to be detected and the level of the risk to be predicted become lower.

In step S8, the presentation control unit 158 determines whether or not to provide feedback to the user (target user). Feedback to the target user is executed at a predetermined timing. For example, feedback is executed at a timing such as when a request for feedback is transmitted from the user terminal portion 11 of the target user, every time a predetermined period has elapsed and when a critical risk is predicted. The presentation control unit 158 then determines to provide feedback to the target user in a case where it is a timing for providing feedback to the target user, and the processing proceeds to step S9.

In step S9, the server 13 provides feedback to the user (target user). Specifically, the presentation control unit 158 generates feedback information to be presented to the target user. This feedback information includes one or more among, for example, the driving diagnosis result of the target user, content of the predicted risk, basis of the driving diagnosis result or basis of prediction of the risk, and a proposal for avoiding the risk (hereinafter, referred to as a risk avoidance proposal). The presentation control unit 158 transmits the generated feedback information to the user terminal portion 11 of the target user via the communication unit 151.

For example, in a case where the mobile terminal 51 of the target user receives feedback information, the output unit 66 of the mobile terminal 51 presents the feedback information to the target user using at least one of visual information (for example, video) or auditory information (for example, speech). Further, for example, in a case where the wearable terminal 52 of the target user receives feedback information, the output unit 83 of the wearable terminal 52 presents the feedback information to the target user using at least one of visual information or auditory information.

For example, in a case where lack of sleep of the target user is estimated, a speech message like "You do not get enough sleep. We recommend you to drive after sleeping a little" is output.

Further, for example, as the driving diagnosis result of the target user, the driving aptitude u is presented with a value on a predetermined scale (for example, on a scale of ten), and the basis thereof is presented.

Further, for example, the estimation result of the state of the target user may be presented. For example, emotional quotient such as delight, anger, sorrow, and pleasure, a level of excitement, and aggressiveness of the target user may be presented with a value on a predetermined scale (for example, on a scale of ten).

Thereafter, the processing proceeds to step S10.

Meanwhile, in step S8, in a case where it is determined not to provide feedback to the target user, the processing in step S9 is skipped, and the processing proceeds to step S10.

In step S10, the state estimating unit 152 determines whether or not the user (target user) starts driving. Specifically, the state estimating unit 152 determines whether or not the target user starts driving on the basis of data received from at least one of the user terminal portion 11 of the target user or the vehicle 12 via the communication unit 151.

The processing of determining start of driving may be performed at any of the user terminal portion 11, the vehicle 12, and the server 13. For example, the mobile terminal 51 may execute the processing of determining start of driving by performing driving recognition processing of the target user or by achieving beacon synchronization with the vehicle 12. Further, for example, measurement equipment integrated with an in-vehicle display device, or the like, of the vehicle 12 may execute the processing of determining start of driving.

Note that, in a case where the user terminal portion 11 or the vehicle 12 performs the determination processing, the determination result is included in data transmitted from the user terminal portion 11 or the vehicle 12, and the state estimating unit 152 determines whether or not the target user starts driving on the basis of the determination result.

Then, in a case where it is determined that the target user does not start driving, the processing returns to step S2. Thereafter, in step S10, until it is determined that the target user starts driving, processing from step S2 to step S10 is repeatedly executed. By this means, driving diagnosis of the target user, risk prediction, and damage prediction are performed as appropriate, and adjustment of the detection parameters of dangerous driving and feedback to the target user are performed on the basis of the results. Further, the normal state pattern of the target user and the user aggregate state pattern are updated as appropriate.

Meanwhile, in step S10, in a case where it is determined that the target user starts driving, the processing proceeds to step S11.

In step S11, the server 13 starts processing of estimating the state of the user (target user) during driving. This estimation processing largely differs from the estimation processing in step S1 in that the estimation processing is performed on the basis of the data transmitted from the vehicle 12 in addition to the data from the user terminal portion 11 of the target user.

For example, a line of sight, blink, expression, or the like, of the target user is detected on the basis of video data from the vehicle 12, and is used for estimating a degree of concentration, a level of wakefulness, a degree of fatigue, feeling, or the like, of the target user. Further, for example, content of driving operation, or the like, of the target user is estimated on the basis of vehicle data from the vehicle 12.

Still further, for example, the state of the target user is estimated on the basis of a traveling route of the vehicle 12 and a time slot in which the target user is driving. For example, in a case where the target user drives after a heart rate and an exercise amount of the target user rapidly increase, or in a time slot different from a normal time slot (for example, at midnight or in the early morning), or in a case where the vehicle 12 travels outside a daily living range of the target user, it is estimated that the target user may be irritated by some kind of emergency incident.

Further, the state estimating unit 152 updates the state data log of the target user and estimated state history as appropriate in a similar manner to the processing in step S1.

In step S12, the peripheral data acquiring unit 153 starts acquiring peripheral data of the vehicle 12. For example, the peripheral data acquiring unit 153 detects a structure, a road, congestion, climate, or the like, around the vehicle 12 of the target user on the basis of location information transmitted from the user terminal portion 11 or the vehicle 12, map information received from other servers, or the like, via the communication unit 151, or the like. Further, for example, the peripheral data acquiring unit 153 detects an object (such as, for example, a vehicle, a person, an obstacle, a structure, a road, a traffic light, a traffic sign, and a sign on the road) around the vehicle 12 on the basis of video data, speech data, sensor data, or the like, transmitted from the user terminal portion 11 or the vehicle 12. Note that the user terminal portion 11 or the vehicle 12 may perform processing of detecting objects around the vehicle 12 and transmit a detection result to the server 13.

The peripheral data acquiring unit 153 supplies the acquired peripheral data of the vehicle 12 to the diagnosis unit 154 and the risk predicting unit 156.

In step S13, the server 13 starts processing of detecting driving behavior. Specifically, for example, the following processing is started.

The driving behavior detecting unit 155 acquires data regarding driving behavior (for example, behavior of the target user or the vehicle 12 during driving) among the data received by the communication unit 151 from the user terminal portion 11 of the target user and the vehicle 12, from the communication unit 151. Further, the driving behavior detecting unit 155 detects driving behavior using the driving behavior detection model of the target user stored in the storage unit 162 on the basis of the acquired data regarding driving behavior, the estimated state history of the target user stored in the storage unit 162, and the peripheral data of the vehicle 12 acquired from the peripheral data acquiring unit 153. That is, behavior of the target user and behavior of the vehicle 12 during driving are detected. For example, speed, acceleration, deceleration, brake operation, a steering angle, a traveling route, or the like, of the vehicle 12 is detected.

Note that part of the behavior of the target user during driving may be detected (estimated) by the state estimating unit 152 in step S11.

Further, detection of driving behavior may be performed at any of the user terminal portion 11, the vehicle 12, and the server 13, and may be shared among the user terminal portion 11, the vehicle 12, and the server 13.

The driving behavior detecting unit 155 then performs processing of detecting dangerous driving on the basis of the detected driving behavior, the estimated state history of the target user, and the peripheral data of the vehicle 12.

For example, sudden operation is detected from sudden fluctuation of speed, the steering angle, torque, or the like, of the vehicle 12 based on the OBD information, or the like, or sudden fluctuation of acceleration, angular velocity, or the like, detected by the user terminal portion 12.

For example, driving in zigzag is detected from periodical fluctuation of speed, a steering angle, torque, or the like, of the vehicle 12 based on the OBD information, or the like, or periodical fluctuation of acceleration, angular velocity, or the like, detected by the user terminal portion 12.

For example, lack in a distance between cars is detected from a location of a preceding car detected using a stereo camera, a laser radar, or a millimeter wave radar.

Here, the detection parameters adjusted in step S7 described above or in step S20 which will be described later are used for the processing of detecting dangerous driving. Therefore, as described above, as the driving aptitude u of the target user becomes lower, a level of dangerous driving to be detected becomes lower, so that a detection target is detected as dangerous driving in an earlier and minor stage.

The driving behavior detecting unit 155 stores a detection result of driving behavior in the storage unit 162 along with time at which the driving behavior is detected. By this means, the driving behavior history of the target user is updated.

In step S14, the diagnosis unit 154 diagnoses driving during driving. For example, the diagnosis unit 154 corrects the driving aptitude u using the driving diagnosis model of the target user stored in the storage unit 162 on the basis of the estimated state history and the driving behavior history of the target user after the user starts driving.

For example, in a case where the degree of concentration or the level of wakefulness of the target user is lowered, or the degree of fatigue, the stress level, or the tension level of the target user increases, the driving aptitude u is lowered. Meanwhile, for example, in a case where the degree of concentration or the level of wakefulness of the target user increases or the degree of fatigue, the stress level, or the tension level of the target user is lowered, the driving aptitude u is increased. Further, for example, in a case where dangerous driving is detected, the driving aptitude u is lowered in accordance with detection frequency. Meanwhile, in a case where a state where dangerous driving is not detected continues, the driving aptitude u is increased in accordance with a duration.

Note that the driving aptitude u may be corrected on the basis of whether driving operation of the target user is good or bad, such as smoothness of stepping-in of a brake pedal and an accelerator pedal, a manipulating way of a steering wheel at cornering, and smoothness of acceleration and deceleration.

The diagnosis unit 154 stores the corrected driving aptitude u and the estimated cause of lowering in the storage unit 162 as the diagnosis result of driving aptitude of the target user along with time at which the diagnosis is made. By this means, the driving diagnosis history of the target user is updated.

In step S15, the risk predicting unit 156 predicts a risk. Here, the risk predicting unit 156 predicts a risk further using the estimated state history and the driving behavior history of the target user stored in the storage unit 162 in addition to the driving diagnosis history of the target user unlike with the processing in step S5. For example, even if the driving aptitude u of the target user is high, as detection frequency of dangerous driving becomes higher and as a degree of risk of the detected dangerous driving becomes higher, the predicted risk becomes greater. Meanwhile, for example, even if the driving aptitude u of the target user is low, in a case where dangerous driving is not detected, the predicted risk becomes smaller. In this manner, because a risk is predicted further using an actual state and driving behavior of the target user during driving, accuracy of risk prediction is improved compared to the processing in step S5.

Further, the risk predicting unit 156 can also predict time at which the probability of occurrence of a risk becomes higher in the future (hereinafter, risk increase time) as well as a risk and the probability of occurrence of the risk. For example, the risk predicting unit 156 estimates time at which the degree of concentration, the tension level, or the level of wakefulness of the target user falls below predetermined thresholds as the risk increase time on the basis of time-series change of the degree of concentration, the tension level, or the level of wakefulness of the target user.

The risk predicting unit 156 supplies a prediction result of the risk to the damage predicting unit 157. This prediction result of the risk includes content of the predicted risk, a basis of prediction of the risk (for example, a cause of lowering of the driving aptitude u and a detection result of dangerous driving), and the probability of occurrence of the risk. Further, the prediction result includes the risk increase time as necessary.

In step S16, in a similar manner to the processing in step S6, damage is predicted. However, the damage predicting unit 157 predicts damage further using the level of obedience of the target user unlike with the processing in step S6. That is, as the level of obedience of the target user is higher, a possibility that a risk is avoided becomes higher, and, as the level of obedience is lower, a possibility that a risk is avoided becomes lower. Therefore, as the level of obedience is higher, the predicted damage becomes smaller, and, as the level of obedience is lower, the predicted damage becomes greater. The damage predicting unit 157 supplies prediction results of a risk and a damage to the driving behavior detecting unit 155 and the presentation control unit 158.

Here, the level of dangerous driving to be detected and the level of the risk to be predicted change in accordance with the level of obedience of the target user. For example, as described above, as the level of obedience of the target user becomes lower, the predicted damage of the risk becomes greater. Therefore, the detection parameters are adjusted so that the level of dangerous driving to be detected becomes further lower. As a result, as the level of obedience becomes lower, the level of dangerous driving to be detected and the level of the risk to be predicted become lower.

In step S17, the presentation control unit 158 determines whether or not to provide feedback to the user (target user). For example, in a case where occurrence of a risk which the target user is required to be notified of is predicted, the presentation control unit 158 determines to provide feedback to the target user, and the processing proceeds to step S18.

In step S18, in a similar manner to the processing in step S8, feedback is provided to the target user. Here, a specific example of the feedback information to be presented to the target user will be described.

For example, in a case where lack of sleep of the target user is estimated, attention is called to dangerous driving when sudden operation or driving in zigzag is detected. For example, a speech message like "You do not get enough sleep. Please drive carefully" is output at the user terminal portion 11 of the target user or the vehicle 12. For example, part of "Please drive carefully" is the risk avoidance proposal, and "You do not get enough sleep" is a basis for presenting the risk avoidance proposal.

For example, in a case where it is estimated that the target user is located outside a daily living range, or in a case where it is estimated that the target user feels intense stress, attention is called to dangerous driving when approach to the preceding vehicle is detected. For example, at the user terminal portion 11 of the target user or the vehicle 12, a speech message like "Are you in a hurry? Let's drive calmly" is output. For example, part of "Let's drive calmly" is the risk avoidance proposal, and part of "Are you in a hurry?" is a basis for presenting the risk avoidance proposal.

For example, in a case where it is estimated that the target user has exercised hard before driving, when it is detected that a line of sight of the target user focusing on one point, or when a number of pedestrians are detected around the vehicle 12, attention is called to a possibility of dangerous driving. For example, at the user terminal portion 11 of the target user or the vehicle 12, a speech message like "Are you sleepy? Please drive while being aware of your surroundings" is output. For example, part of "Please drive while being aware of your surroundings" is the risk avoidance proposal, and part of "Are you sleepy?" is a basis for presenting the risk avoidance proposal.

For example, in a case where it is estimated that the target user is located outside a daily living range, or in a case where it is estimated that the target user does not get enough sleep, when sudden operation or driving in zigzag is detected while the target user is driving on a highway, attention is called to dangerous driving. For example, at the user terminal portion 11 of the target user or the vehicle 12, a speech message like "Why don't you take a rest at the next service area? You did not get enough sleep yesterday, and you are now driving in zigzag" is output. For example, part of "Why don't you take a rest at the next service area?" is the risk avoidance proposal, and part of "You did not get enough sleep yesterday, and you are now driving in zigzag" is a basis for presenting the risk avoidance proposal.

For example, in a case where it is estimated the target user does not get enough sleep or is in a state of extremely high tension, when dangerous driving is frequently detected, attention is called to increase in an insurance fee of an automobile insurance, and a cause of the increase is presented. For example, at the user terminal portion 11 of the target user or the vehicle 12, a speech message like "You frequently drive dangerously due to lack of sleep (or tension). If dangerous driving is detected more x times, right of cashback of an insurance fee will be lost" is output. For example, part of "If dangerous driving is detected more x times, right of cashback of an insurance fee will be lost" is a warning to the target user, and part of "You frequently drive dangerously due to lack of sleep (or tension)" is a basis for the warning.

For example, in a case where it is estimated that the target user travels on an unfamiliar road outside a daily living range, and the risk increase time due to fatigue is estimated, a speech message like "Aren't you tired? Why don't you take a rest at service area A?" is output. Note that the service area A is a service area which is estimated to be reachable by the vehicle 12 of the target user by the risk increase time. For example, part of "Why don't you take a rest at service area A?" is the risk avoidance proposal, and part of "Aren't you tired?" is a basis for presenting the risk avoidance proposal.

Note that the risk avoidance proposal can be made more specific content, for example, like "Please reduce speed to 60 km/h", "Please face the front immediately", or the like.

Further, the presentation control unit 158 supplies the feedback information to the evaluating unit 159.

In step S19, the evaluating unit 159 evaluates the level of obedience of the user (target user). Specifically, the evaluating unit 159 acquires the estimated state history and the driving behavior history of the target user after feedback is provided to the target user, from the storage unit 162. The evaluating unit 159 then detects response (for example, content of driving) of the target user to the feedback on the basis of the acquired history.

Further, the evaluating unit 159 updates an evaluation value of the level of obedience of the target user on the basis of the response of the target user. For example, in a case where the feedback information presented this time includes the risk avoidance proposal, and the target user follows the risk avoidance proposal, the level of obedience of the target user increases. Further, as a period until the target user follows the risk avoidance proposal is shorter (response speed is faster), or as a difference between response of the target user and the risk avoidance proposal is smaller, an increase of the level of obedience of the target user becomes greater. Inversely, as the period until the target user follows the risk avoidance proposal is longer (response speed is slower), or as the difference between the response of the target user and the risk avoidance proposal is larger, the increase of the level of obedience of the target user becomes smaller.

Meanwhile, in a case where the target user does not follow the risk avoidance proposal, for example, in a case where the target user ignores the risk avoidance proposal, or in a case where the target user responds differently from the risk avoidance proposal, the level of obedience of the target user is lowered. Particularly, in a case where the target user drives dangerously without following the risk avoidance proposal, a decrease of the level of obedience of the target user becomes greater.

The evaluating unit 159 supplies the uprated level of obedience of the target user to the damage predicting unit 157 and stores the updated level of obedience of the target user in the storage unit 162.

Thereafter, the processing proceeds to step S20.

Meanwhile, in a case where it is determined in step S17 that feedback is not provided to the target user, the processing in step S18 and step S19 is skipped, and the processing proceeds to step S20.

In step S20, the detection parameters of driving behavior are adjusted in a similar manner to the processing in step S7.

In step S21, the state estimating unit 152 determines whether or not the user stops driving. That is, the state estimating unit 152 determines whether or not the target user stops driving on the basis of data received from at least one of the user terminal portion 11 of the target user or the vehicle 12 via the communication unit 151 in a similar manner to the processing of determining start of driving in step S10.

Then, in a case where it is determined that the target user does not stop driving, the processing returns to step S14. Thereafter, until it is determined in step S21 that the target user stops driving, the processing from step S14 to step S21 is repeatedly executed. By this means, driving diagnosis of the target user, risk prediction, and damage prediction are performed as appropriate, and adjustment of the detection parameters of dangerous driving and feedback to the target user are performed on the basis of the results. Further, the level of obedience of the target user is updated as appropriate.

Meanwhile, in a case where it is determined in step S21 that the target user stops driving, the processing proceeds to step S22.

In step S22, processing of estimating the state of the target user while the target user is not driving is started in a similar manner to the processing in step S1.

In step S23, the peripheral data acquiring unit 153 stops acquisition of peripheral data of the vehicle 12.

In step S24, the driving behavior detecting unit 155 stops processing of detecting driving behavior.

In step S25, the learning unit 160 performs learning processing. For example, the learning unit 160 learns the state estimation model, the driving diagnosis model, the driving behavior detection model, and the risk prediction model on the basis of the state data log, the estimated state history, the driving diagnosis history, and the driving behavior history of the target user stored in the storage unit 162.

For example, in a case where safe driving is performed although the driving aptitude u is evaluated as low, the weight wx and the weight wy in the above-described expression (1) indicating the driving diagnosis model are set smaller. By this means, the driving aptitude u of the target user is evaluated as higher than that evaluated before. Inversely, in a case where dangerous driving is frequently performed although the driving aptitude u is evaluated as high, the weight wx and the weight wy in the expression (1) are set greater. By this means, the driving aptitude u of the target user is evaluated as lower than that evaluated before.

Further, for example, in a case where safe driving is performed although a difference between the most recent state pattern of the target user and the user aggregate state pattern is large, and the driving aptitude u is evaluated as low, the weight wx in the above-described expression (1) is set greater, and the weight wy is set smaller. That is, in the driving diagnosis, more emphasis is put on the difference between the most recent state pattern of the target user and the normal state pattern.

Note that, for example, at the beginning when the target user starts utilizing service, a model corresponding to an average user obtained through experiments, or the like, performed in advance is used. Thereafter, through learning processing, each model is updated (personalized) to a model more suitable for the target user.

Note that this learning processing does not necessarily have to be performed every time driving of the target user is finished, and may be performed at an arbitrary timing such as, for example, for each predetermined period, every time driving is performed a predetermined number of times, and every time a driving period increases by equal to or longer than a predetermined period. Further, learning processing does not necessarily have to be performed at the same time for all the models, and learning processing may be performed at timings different for each model.

Further, for example, the learning unit 160 may learn a fatigue degree estimation model for predicting the degree of fatigue of the target user on the basis of transition of the degree of fatigue of the target user before driving and during driving indicated in the estimated state history. For example, the state estimating unit 152 can estimate the degree of fatigue of the target user at each point of a traveling scheduled route using the fatigue degree estimation model. Still further, for example, by the learning unit 160 learning the fatigue degree estimation model while taking into account a state around the vehicle 12 such as a time slot, climate, a state of congestion, and a type of a road (for example, a general road or a highway), it is possible to improve estimation accuracy of the degree of fatigue.

Further, as a method for learning processing, for example, machine learning such as a neural network and other arbitrary methods can be used.

In step S26, the insurance fee calculating unit 161 calculates an insurance fee of the user (target user). For example, in a case where an insurance fee of the automobile insurance of the target user or a cashback amount for the insurance fee fluctuates in real time, the insurance fee calculating unit 161 updates the insurance fee or the cashback amount on the basis of the driving diagnosis history, the driving behavior history, and the level of obedience of the target user stored in the storage unit 162. The insurance fee calculating unit 161 stores the updated insurance fee or cashback amount of the target user in the storage unit 162.

For example, as an average value of the driving aptitude u is lower, the insurance fee increases (or the cashback amount degreases), while, as the average value of the driving aptitude u is higher, the insurance fee degreases (or the cashback amount increases).

Further, for example, as frequency or the cumulative number of times of dangerous driving is greater, the insurance fee increases (or the cashback amount decreases), while, as the frequency or the cumulative number of times of dangerous driving is smaller, the insurance fee decreases (or the cashback amount increases). Still further, for example, as an average or a sum of damage predicted for dangerous driving is higher, the insurance fee increases (or the cashback amount decreases), while, as the average or the sum of damage predicted for dangerous driving is lower, the insurance fee decreases (or the cashback amount increases).

Further, for example, as the level of obedience is lower, the insurance fee increases (or the cashback amount decreases), because lowering of the risk cannot be expected, while, as the level of obedience is higher, the insurance fee decreases (or the cashback amount increases), because lowering of the risk can be expected. Particularly, in a case where the target user drives dangerously without following the risk avoidance proposal, for example, an increase of the insurance fee (or a decrease of the cashback amount) becomes greater as penalty.

Note that this insurance fee calculation processing does not necessarily have to be performed every time driving of the target user is finished, and may be performed at an arbitrary timing such as, for example, for each predetermined period, every time driving is performed a predetermined number of times, and every time a driving period increases by equal to or longer than a predetermined period.

Further, this insurance fee calculation processing may be, for example, executed for calculating an estimate of the insurance fee when the insurance is updated next time.

Still further, for example, in a case where the insurance is an automobile insurance for each time of driving or on a day-to-day basis, the insurance fee may be calculated by executing this insurance fee calculation processing before driving. In this case, for example, the insurance fee is calculated using at least one of the driving aptitude u or the level of obedience of the target user.

Further, the calculated insurance fee or cashback amount may be presented to the target user as the feedback information.

Thereafter, the processing returns to step S2, and processing in step S2 and subsequent processing are executed.

For example, driving behavior is affected by the state of the user before driving (such as, for example, behavior, a biological state, and feeling) as well as the state of the user during driving. In contrast, as described above, by multiply taking into account the state of the user before driving in addition to the state and the driving behavior of the user during driving, the driving aptitude u is evaluated more appropriately. Further, by accuracy of the driving aptitude u being improved, accuracy of risk prediction and damage prediction is improved. As a result, it is possible to present appropriate feedback information at a more appropriate timing, so that it is possible to improve safety and prevent occurrence of an accident.

Further, because a basis for a result of the driving diagnosis or a basis for predicting the risk is indicated in the feedback information, the user is more convinced, so that a probability that the user follows the risk avoidance proposal increases. Further, in a case where the presented basis is wrong, for example, by the user instructing the server 13 to correct the basis and reflect the correction on learning processing, accuracy of the driving diagnosis model and the risk prediction model is improved.

Still further, as a result of the level of obedience of the user being evaluated and a level of dangerous driving to be detected and a level of a risk to be predicted changing on the basis of the level of obedience, the user can avoid a risk more reliably.

Further, by the insurance fee (including the cashback amount) of the automobile insurance being calculated on the basis of the driving aptitude u and the level of obedience as well as the driving behavior of the user, it is possible to set a more appropriate insurance fee for each user. By this means, for example, the user can be motivated to follow the risk avoidance proposal, so that the user can avoid a risk more reliably.

2. Modified Examples

Modified examples of the embodiment of the technology according to the present disclosure described above will be described below.

Modified Example Relating to System Configuration

A configuration example of the information processing system 10 in FIG. 1 to FIG. 4 is an example, and can be changed as necessary.

For example, while, in the above description, an example has been described where the server 13 performs most processing on the basis of data acquired from the user terminal portion 11 and the vehicle 12 (in-vehicle system 101), for example, the processing can be shared among the user terminal portion 11, the vehicle 12, and the server 13, or the processing may be performed by the user terminal portion 11 alone or by the vehicle 12 alone.

For example, at least one of the user terminal portion 11 or the vehicle 12 can perform part or all of the processing of the server 13.

For example, at least one of the user terminal portion 11 or the vehicle 12 may perform part or all of the processing of the state estimating unit 152, the driving behavior detecting unit 155, and the evaluating unit 159 and may transmit the estimation result and the detection result to the server 13.

For example, at least one of the user terminal portion 11 or the vehicle 12 may perform part or all of the processing of the peripheral data acquiring unit 153 and may transmit the acquired peripheral data to the server 13.

For example, at least one of the user terminal portion 11 or the vehicle 12 may perform part or all of the processing of the diagnosis unit 154, the risk predicting unit 156, and the damage predicting unit 157 and may transmit the diagnosis result and the prediction result to the server 13.

Further, for example, the processing regarding driving assistance may be performed at the user terminal portion 11. In this case, the user terminal portion 11 may be configured with a plurality of devices or may be configured with a single device. Further, the user terminal portion 11 may acquire various kinds of data (such as, for example, vehicle data, video data, and speech data) from the vehicle 12 and may use the data in the processing or does not have to use the data from the vehicle 12 in the processing. Further, the user aggregate state pattern may be used or does not have to be used in driving diagnosis processing. In a case where the user aggregate state pattern is used, for example, the server 13 learns the user aggregate state pattern on the basis of the normal state patterns of the respective users acquired from the user terminal portions 11 of the respective users. The server 13 then transmits data indicating the user aggregate state pattern to the user terminal portions 11 of the respective users.

In this case, the processing of calculating the insurance fee may be performed at any of the user terminal portion 11 and the server 13. In a case where the processing is performed at the user terminal portion 11, for example, an application program for performing processing of calculating the insurance fee is provided from the server 13. Meanwhile, in a case where the processing is performed at the server 13, for example, data required for calculating the insurance fee is provided from the user terminal portion 11 to the server 13.

Still further, for example, among the processing regarding driving assistance, almost all kinds of processing except the processing of estimating the state of the user while the user is not driving and the processing of learning the normal state pattern may be performed at the vehicle 12 (in-vehicle system 101). In this case, for example, the user terminal portion 11 performs the processing of estimating the state of the user while the user is not driving and the processing of learning the normal state pattern, and transmits data indicating the estimated state history and the normal state pattern obtained as a result to the vehicle 12 before driving. The vehicle 12 then executes the remaining processing. In this case, the user aggregate state pattern may be used or does not have to be used in the driving diagnosis processing. In a case where the user aggregate state pattern is used, in a case where the user aggregate state pattern is used, for example, the server 13 learns the user aggregate state pattern on the basis of normal state patterns of the respective users acquired from the user terminal portions 11 of the respective users. The server 13 then transmits data indicating the user aggregate state pattern to the user terminal portions 11 or the vehicles 12 of the respective users.

In this case, the processing of calculating the insurance fee may be performed at any of the user terminal portion 11, the vehicle 12, and the server 13. In a case where the processing is performed at the user terminal portion 11 or the vehicle 12, for example, an application program for performing the processing of calculating the insurance fee is provided from the server 13. Meanwhile, in a case where the processing is performed at the server 13, for example, data required for calculating the insurance fee is provided from the user terminal portion 11 and the vehicle 12 to the server 13.

Further, for example, the processing may be shared between the user terminal portion 11 and the server 13. In this case, data from the vehicle 12 may be used or does not have to be used in the processing.

Still further, for example, the processing may be shared between the vehicle 12 and the server 13. In this case, for example, data required for the processing (such as, for example, the normal state pattern and the most recent state pattern of the user) is provided from the user terminal portion 11 to the vehicle 12 and the server 13.

Further, for example, the processing may be shared among a plurality of servers. For example, the processing regarding driving assistance and the processing regarding calculation of the insurance fee may be performed at different servers.

Further, for example, communication between the vehicle 12 and the server 13 may be performed via the user terminal portion 11. In this case, for example, after data from the vehicle 12 is transmitted to the user terminal portion 11 once, the data is transferred from the user terminal portion 11 to the server 13. Further, after data from the server 13 is transmitted to the user terminal portion 11 once, the data is transferred from the user terminal portion 11 to the vehicle 12.

Further, for example, communication between the user terminal portion 11 and the server 13 may be performed via the vehicle 12. In this case, for example, after data from the user terminal portion 11 is transmitted to the vehicle 12 once, the data is transferred from the vehicle 12 to the server 13. Further, after data from the server 13 is transmitted to the vehicle 12 once, the data is transferred from the vehicle 12 to the user terminal portion 11.

Further, for example, in place of the estimated state history, driving diagnosis of the diagnosis unit 154, risk prediction by the risk predicting unit 156, and detection of driving behavior by the driving behavior detecting unit 155 may be performed directly using the state data log before the state of the user is estimated. In this case, it is possible to delete the state estimating unit 152.

Other Modified Examples

For example, the driving aptitude u may be calculated using a current state of the user in addition to the degree of divergence between the most recent state pattern of the user and the normal state pattern or the user aggregate average pattern. For example, even if a difference between the most recent state pattern of the user and the normal state pattern is small, there is a high possibility that dangerous driving is performed, for example, in a case where the level of wakefulness of the user is low, or the user is excited or gets depressed. Therefore, for example, among respective items indicating the states of the user, concerning items which largely affect driving, current states (for example, the level of wakefulness, the level of excitement, the level of depression) of these items may be used for calculating the driving aptitude u.

Further, the estimated state of the user is not limited to three types of the biological state, the behavior, and the feeling described above. For example, it is also possible to estimate only one or two types among the above-described three types or estimate other types of states.

Still further, for example, it is also possible to use behavior of the user which is normally not assumed to directly affect driving, for calculating the driving aptitude u. For example, in a case where the user buys something different from normal tendency on the basis of purchasing history of the user (for example, in a case where the user buys an extremely expensive item), it is assumed that the state of the user (for example, feeling) is different from a normal state. Therefore, for example, the purchasing history of the user may be used for calculating the driving aptitude u.

Further, for example, ability of the user which is detected on the basis of the state of the user while the user is not driving and which is ability which also affects driving may be used for calculating the driving aptitude u. For example, it is also possible to set higher driving aptitude u of the user who is competent in daily life and set lower driving aptitude u of the user who is less competent.

Note that, in this case, for example, even if a user who is competent and a user who is less competent frequently repeat lane changing in a similar manner, a risk predicted for the user who is competent becomes lower, and a risk predicted for the user who is less competent becomes higher. However, even if the user is competent, in a case where the user repeats lane changing while ignoring the presented risk avoidance proposal for reducing lane changing, because the level of obedience is evaluated as low, the predicted risk becomes higher.

Further, for example, it is also possible to predict a risk on the basis of only one or two results among the estimation result of the state of the user, the result of driving diagnosis and the detection result of driving behavior. Further, for example, in a case where a risk is predicted using the result of driving diagnosis, only one of the driving aptitude u before driving and the driving aptitude u during driving may be used.

Further, for example, driving diagnosis may be performed on the basis of only one of the state of the user before driving and the state of the user during driving.

Still further, for example, it is also possible to use the estimated state history, the driving diagnosis history, and the driving behavior history to investigate a cause of occurrence of the accident. For example, by the estimated state history, the driving diagnosis history and the driving behavior history being recorded in a dashboard camera, it is possible to investigate a cause of occurrence of the accident on the basis of the state of the user before driving in addition to the state and behavior of the user (driver) when the accident occurs.

Further, for example, the user terminal portion 11 or the vehicle 12 may be able to acquire driving aptitude u, a result of risk prediction of other users, and the like from user terminal portions 11 or vehicles 12 of other users or the server 13. By this means, for example, in a case where a dangerous vehicle driven by a user who has low driving aptitude u is located near, for example, the user can avoid himself/herself from being involved with an accident by the dangerous vehicle by acquiring the information in advance.

Still further, it is not necessarily required to personalize the state estimation model, the driving diagnosis model, the driving behavior detection model, and the risk prediction model, and it is also possible to use a model which uses predetermined algorithm, or the like. Further, for example, the above-described learning of the model may be performed, for example, as a whole of the user aggregate without being performed for each user, and the respective users may use a common model.

Further, for example, a method for presenting the feedback information, presentation frequency, presented content, or the like, may be changed on the basis of the level of obedience of the user.

Application Examples

The driving assistance processing of the present technology can be applied in a case of driving of various kinds of mobile bodies such as a motorbike, a bicycle, a personal mobility, an airplane, a ship, construction machine, and agricultural machine (tractor), as well as the vehicles described above, for example. That is, it is possible to diagnose driving, predict a risk, predict damage, provide feedback, or the like, to the user using the estimation results of the state of the user before driving and during driving. Note that mobile bodies to which the present technology can be applied include a mobile body in which part which works moves at a fixed location, such as part of construction machine, or the like, (such as, for example, a stationary crane) as well as mobile bodies which move locations. Further, the mobile bodies to which the present technology can be applied include a mobile body which is remotely operated (manipulated) by the user without the user getting on the mobile body, such as, for example, a drone and a robot.

Further, the present technology can be applied to a system, an apparatus, or the like, which provide various kinds of insurances such as a life insurance, a property insurance, and a health insurance as well as an automobile insurance. For example, it is possible to calculate various kinds of insurance fees (including a cashback amount) on the basis of the estimated state history and the level of obedience of the user. Specifically, for example, in a case of a life insurance or a health insurance, the user terminal portion 11 or the server 13 performs processing of estimating the state of the user and accumulates the estimated state history. Further, the user terminal portion 11 or the server 13 presents a proposal (risk avoidance proposal) for avoiding a risk such as a disease on the basis of a lifestyle, the biological state, or the like, of the user based on the estimated state history, to the user, and evaluates the level of obedience of the user on the basis of response to the presentation. The user terminal portion 11 or the server 13 then calculates an insurance fee of the life insurance or the health insurance on the basis of the lifestyle and the biological state of the user, the level of obedience, or the like.

For example, the insurance fee becomes lower for a user whose lifestyle and biological state are more favorable, and the insurance fee becomes higher for a user whose lifestyle and biological state are worse. Further, the insurance fee becomes lower for the user whose level of obedience is higher, and the insurance fee becomes higher for the user whose level of obedience is lower. In this manner, it is possible to set a more appropriate insurance fee for each user in a similar manner to the above-described case of the automobile insurance by taking into account the level of obedience of the user as well as the lifestyle and the biological state of the user.

3. Others

Example of Computer Configuration

Incidentally, the above-described series of processes may be performed by hardware or may be performed by software. In a case where the series of processes are performed by software, a program forming the software is installed into a computer. Here, examples of the computer include a computer that is incorporated in dedicated hardware, a general-purpose personal computer that can perform various types of function by installing various types of program, and the like.

Figure 11:
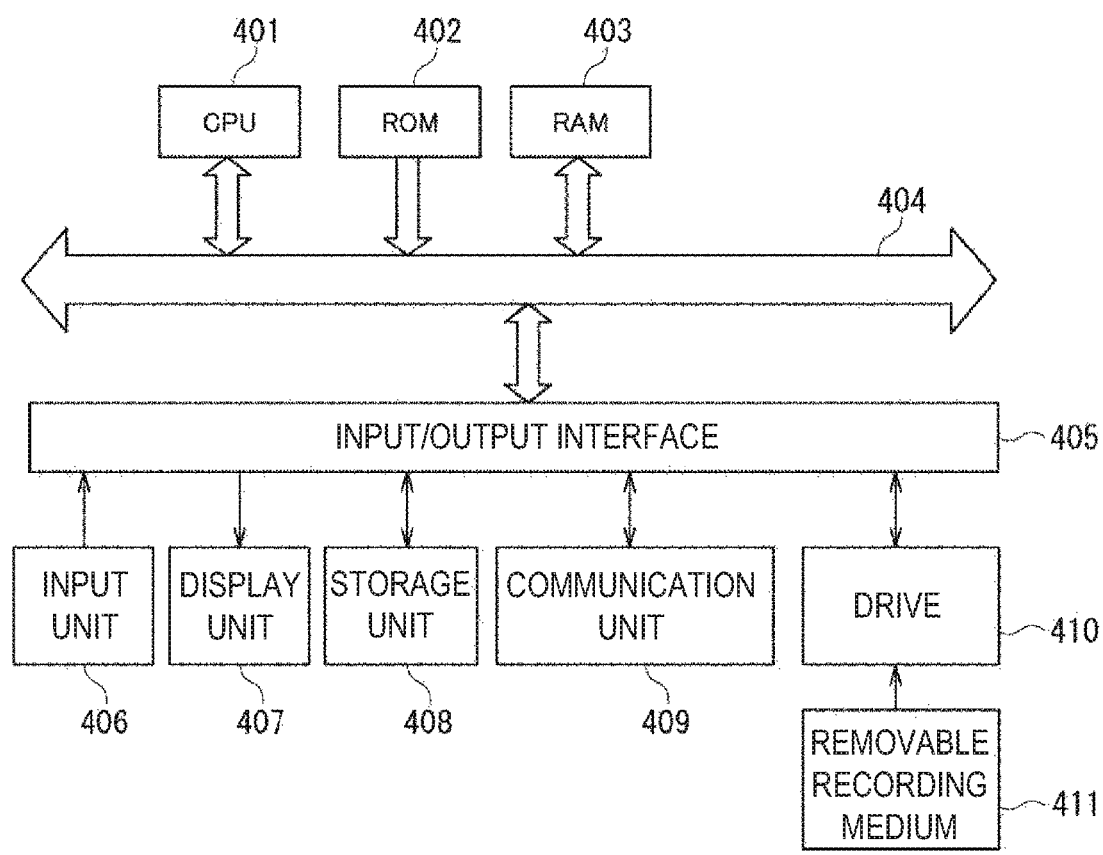
FIG. 11 is a diagram illustrating a configuration example of a computer.

FIG. 11 is a block diagram illustrating a configuration example of the hardware of a computer that performs the above-described series of processes with a program.

In the computer, a central processing unit (CPU) 401, read only memory (ROM) 402, and random access memory (RAM) 403 are mutually connected by a bus 404.

Further, an input/output interface 405 is connected to the bus 404. Connected to the input/output interface 405 are an input unit 406, an output unit 407, a recording unit 408, a communication unit 409, and a drive 410.

The input unit 406 includes an input switch, a button, a mouse, a microphone, an image sensor, and the like. The output unit 407 includes a display, a speaker array, and the like. The recording unit 408 includes a hard disk, a non-volatile memory, and the like. The communication unit 409 includes a network interface, and the like. The drive 410 drives a removable recording medium 411 such as a magnetic disk, an optical disc, a magneto-optical disk, and a semiconductor memory.

In the computer configured as described above, the CPU 401 loads a program that is recorded, for example, in the recording unit 408 onto the RAM 403 via the input/output interface 405 and the bus 404, and executes the program, thereby performing the above-described series of processes.

For example, programs to be executed by the computer (CPU 401) can be recorded and provided in the removable recording medium 411, which is a packaged medium or the like. In addition, programs can be provided via a wired or wireless transmission medium such as a local area network, the Internet, and digital satellite broadcasting.

In the computer, by mounting the removable recording medium 411 onto the drive 410, programs can be installed into the recording unit 408 via the input/output interface 405. Further, programs can also be received by the communication unit 409 via a wired or wireless transmission medium, and installed into the recording unit 408. In addition, programs can be installed in advance into the ROM 402 or the recording unit 408.

Note that a program executed by the computer may be a program in which processes are chronologically carried out in a time series in the order described herein or may be a program in which processes are carried out in parallel or at necessary timing, such as when the processes are called.

Further, in this specification, a system has the meaning of a set of a plurality of structural elements (such as an apparatus or a module (part)), and does not take into account whether or not all the structural elements are in the same casing. Therefore, the system may be either a plurality of apparatuses stored in separate casings and connected through a network, or an apparatus in which a plurality of modules is stored within a single casing.

Further, an embodiment of the present technology is not limited to the embodiments described above, and various changes and modifications may be made without departing from the scope of the present technology.

For example, the present technology can adopt a configuration of cloud computing, in which a plurality of devices shares a single function via a network and performs processes in collaboration.

Furthermore, each step in the above-described flowcharts can be executed by a single device or shared and executed by a plurality of devices.

In addition, in a case where a single step includes a plurality of processes, the plurality of processes included in the single step can be executed by a single device or shared and executed by a plurality of devices.

Combination Example of Configuration

The present technology may also be configured as below.
(1)
An information processing apparatus including:
a presentation control unit configured to generate a risk avoidance proposal for a user on the basis of a predicted risk;
an evaluating unit configured to evaluate a level of obedience of the user on the basis of response of the user to the risk avoidance proposal; and
a risk predicting unit configured to adjust a risk prediction parameter on the basis of the evaluated level of obedience.

(2)

The information processing apparatus according to (1), in which the risk predicting unit predicts a risk regarding driving of a mobile body by the user.

(3)

The information processing apparatus according to (2), further including:

a driving behavior detecting unit configured to detect driving behavior which is behavior of the user or the mobile body during driving, in which the risk predicting unit predicts the risk on the basis of a detection result of the driving behavior.

(4)

The information processing apparatus according to (3), in which a level of dangerous driving behavior, which is to be detected by the driving behavior detecting unit, changes on the basis of the level of obedience.

(5)

The information processing apparatus according to (4), in which, as the level of obedience becomes lower, the level of dangerous driving behavior, which is to be detected by the driving behavior detecting unit, becomes lower.

(6)

The information processing apparatus according to any one of (2) to (4), further including:

a diagnosis unit configured to diagnose aptitude of the user for driving on the basis of at least one of a state of the user before driving or a state of the user during driving, in which the risk predicting unit predicts the risk on the basis of a result of the diagnosis.

(7)

The information processing apparatus according to any one of (1) to (6), in which, as the level of obedience becomes lower, a level of a risk, which is to be predicted by the risk predicting unit, becomes lower.

(8)

The information processing apparatus according to any one of (1) to (7), further including:

an insurance fee calculating unit configured to calculate an insurance fee of an insurance for the user on the basis of the level of obedience.

(9)

The information processing apparatus according to (8), in which the insurance fee calculating unit lowers the insurance fee as the level of obedience is higher and increases the insurance fee as the level of obedience is lower.

(10)

The information processing apparatus according to (8) or (9), in which the risk is a risk regarding driving of a vehicle by the user, and the insurance includes an automobile insurance.

(11)

An information processing method including:

a presentation control step of generating a risk avoidance proposal for a user on the basis of a predicted risk;

an evaluation step of evaluating a level of obedience of the user on the basis of response of the user to the risk avoidance proposal; and a risk prediction step of adjusting a risk prediction parameter on the basis of the evaluated level of obedience.

(12)

A program for causing a computer to execute processing including:

a presentation control step of generating a risk avoidance proposal for a user on the basis of a predicted risk;

an evaluation step of evaluating a level of obedience of the user on the basis of response of the user to the risk avoidance proposal; and a risk prediction step of adjusting a risk prediction parameter on the basis of the evaluated level of obedience.

Further, the advantageous effects described in the present specification are merely examples and are not limitative, and other advantageous effects may be achieved.

REFERENCE SIGNS LIST

10 Information processing system
11 User terminal portion
12 Vehicle
13 Server
51 Mobile terminal
52 Wearable terminal
61 GNSS receiver
62 Inertial sensor
63 Environment sensor
64 Biological sensor
66 Output unit
67 Control unit
81 Biological sensor
83 Output unit
84 Control unit
101 In-vehicle system
111 Vehicle data acquiring unit
112 Video and speech acquiring unit
114 Output unit
115 Control unit
152 State estimating unit
154 Diagnosis unit
155 Driving behavior detecting unit
156 Risk predicting unit
157 Damage predicting unit
158 Presentation control unit
159 Evaluating unit
160 Learning unit
161 Insurance fee calculating unit

The invention claimed is:

1. An information processing apparatus, comprising:
a risk predicting unit configured to predict a risk associated with driving of a mobile body by a user;
a presentation control unit configured to generate a risk avoidance proposal for the user based on the predicted risk; and
an evaluating unit configured to:
acquire a state history of the user and a driving behavior history of the user based on the generated risk avoidance proposal, wherein
the state history corresponds to a history of a first state of the user at a time of the driving of the mobile body in past, and
the driving behavior history corresponds to one of a behavior of the user while the mobile body is driven in the past or a behavior of the mobile body driven in the past;
determine a response of the user to the risk avoidance proposal based on the acquired state history and the acquired driving behavior history; and
evaluate a level of obedience of the user based on a time interval between the response of the user and the generation of the risk avoidance proposal, wherein the risk predicting unit is further configured to adjust a risk prediction parameter based on the evaluated level of obedience.

2. The information processing apparatus according to claim 1, further comprising a driving behavior detecting unit configured to detect driving behavior which is the behavior of the user or the behavior of the mobile body during the driving of the mobile body, wherein the risk predicting unit is further configured to predict the risk based on the detected driving behavior.

3. The information processing apparatus according to claim 2, wherein the driving behavior detecting unit is further configured to detect a level of dangerous driving behavior of the user based on the level of obedience of the user.

4. The information processing apparatus according to claim 3, wherein the level of dangerous driving behavior decreases based on a decrease in the level of obedience of the user.

5. The information processing apparatus according to claim 1, further comprising a diagnosis unit configured to diagnose aptitude of the user for driving the mobile body, wherein
the aptitude of the user is diagnosed based on at least one of a second state of the user before the driving or a third state of the user during the driving, and
the risk predicting unit is further configured to predict the risk based on the diagnosed aptitude of the user.

6. The information processing apparatus according to claim 1, wherein a level of the risk decreases based on a decrease in the level of obedience of the user.

7. The information processing apparatus according to claim 1, further comprising an insurance fee calculating unit configured to calculate an insurance fee of an insurance for the user based on the level of obedience of the user.

8. The information processing apparatus according to claim 7, wherein the insurance fee calculating unit is further configured to:
decrease the insurance fee based on an increase in the level of obedience; and
increase the insurance fee based on a decrease in the level of obedience.

9. The information processing apparatus according to claim 7, wherein
the risk is a risk associated with driving of a vehicle by the user, and
the insurance includes an automobile insurance.

10. The information processing apparatus according to claim 1, wherein the level of obedience increases based on a decrease in the time interval between the response of the user and the generation of the risk avoidance proposal.

11. An information processing method, comprising:
predicting a risk associated with driving of a mobile body by a user;
generating a risk avoidance proposal for the user based on the predicted risk;
acquiring a state history of the user and a driving behavior history of the user based on the generated risk avoidance proposal, wherein
the state history corresponds to a history of a state of the user at a time of the driving of the mobile body in past, and
the driving behavior history corresponds to one of a behavior of the user while the mobile body is driven in the past or a behavior of the mobile body driven in the past;
determining a response of the user to the risk avoidance proposal based on the acquired state history and the acquired driving behavior history;
evaluating a level of obedience of the user based on a time interval between the response of the user and the generation of the risk avoidance proposal; and
adjusting a risk prediction parameter based on the evaluated level of obedience.

12. A non-transitory computer-readable medium having stored thereon computer executable-instructions that, when executed by a processor, cause the processor to execute operations, the operations comprising:
predicting a risk associated with driving of a mobile body by a user;
generating a risk avoidance proposal for the user based on the predicted risk;
acquiring a state history of the user and driving behavior history of the user based on the generated risk avoidance proposal, wherein
the state history corresponds to a history of a state of the user at a time of the driving of the mobile body in past, and
the driving behavior history corresponds to one of a behavior of the user while the mobile body is driven in the past or a behavior of the mobile body driven in the past;
determining a response of the user to the risk avoidance proposal based on the acquired state history and the acquired driving behavior history;
evaluating a level of obedience of the user based on a time interval between the response of the user and the generation of the risk avoidance proposal; and
adjusting a risk prediction parameter based on the evaluated level of obedience.

* * * * *